United States Patent
Hogan et al.

(10) Patent No.: US 8,771,951 B2
(45) Date of Patent: *Jul. 8, 2014

(54) METHODS FOR PCR AND HLA TYPING USING RAW BLOOD

(75) Inventors: Michael E. Hogan, Tuscan, AZ (US); Georgina Lopez Padilla, Tucson, AZ (US); Melissa R. May, Tucson, AZ (US); Andrew T. Abalos, Tucson, AZ (US); Frederick H. Eggars, Sahuarita, AZ (US); Kevin M. O'Brien, Sahuarita, AZ (US)

(73) Assignee: Genomics USA, Inc., Inverness, IL (US)

( * ) Notice: Subject to any disclaimer, the term of this patent is extended or adjusted under 35 U.S.C. 154(b) by 458 days.

This patent is subject to a terminal disclaimer.

(21) Appl. No.: 12/924,301

(22) Filed: Sep. 24, 2010

(65) Prior Publication Data

US 2011/0117553 A1    May 19, 2011

Related U.S. Application Data

(60) Provisional application No. 61/281,404, filed on Nov. 16, 2009.

(51) Int. Cl.
*C12Q 1/68*    (2006.01)
*C12P 19/34*    (2006.01)

(52) U.S. Cl.
USPC ......................... 435/6.12; 435/91.2

(58) Field of Classification Search
None
See application file for complete search history.

(56) References Cited

PUBLICATIONS

Stanley et al. (Nucleic Acids Research, 2005, 33(20):e180).*
Zhang et al. (Anal Chem, 1999, 71, p. 1138-1145).*
Sullivan et al. (Int J Leg Med, 1992, 105:83-86).*
Dunbar et al. (Appl Environ Microbiol., 2000, 66(7):2943-2950).*
Xu et al. (Clin Chem, 2002, 48(9):1605-1608).*
Noble et al. (Am J Hum Genet, 1996, 59:1134-1148).*
Kimura et al. (Genome Research, 2006, 16(1):55-65).*
Null et al. (Rapid Commun Mass Spectrom, 2003, 17:2699-2706).*
Bu et al. (Journal of Medical Microbiology, 2005, 24:243-248).*
Lau et al. (J Clin Microbiol, 2008, 46(9):3021).*
Carlotti et al. (Journal of Clinical Microbiology, 1997, 35(6):1337-1343).*

* cited by examiner

*Primary Examiner* — Stephanie K Mummert
(74) *Attorney, Agent, or Firm* — Benjamin Aaron Adler

(57) ABSTRACT

Provided are methods for amplifying a gene or RNA or sets thereof of interest using a tandem PCR process. The primers in the first PCR or set of PCR reactions are locus-specific. The primers in the second PCR or set of PCR reactions are specific for a sub-sequence of the locus-specific primers and completely consumed during the secondary PCR amplification. For RNA amplification, the first PCR is reverse transcription and the resulting cDNA(s) provide a template for cRNA synthesis, endpoint PCR or real time PCR. Also provided is a method of allelotyping a gene or set thereof by amplifying the gene(s) using tandem PCR on DNA or RNA comprising the sample, hybridizing the resulting amplicon or sets thereof to probes with sequences of gene-associated allele variations. A detectable signal indicating hybridization corresponds to an allelotype of the gene or a set of allelotypes for the set of genes.

34 Claims, 23 Drawing Sheets

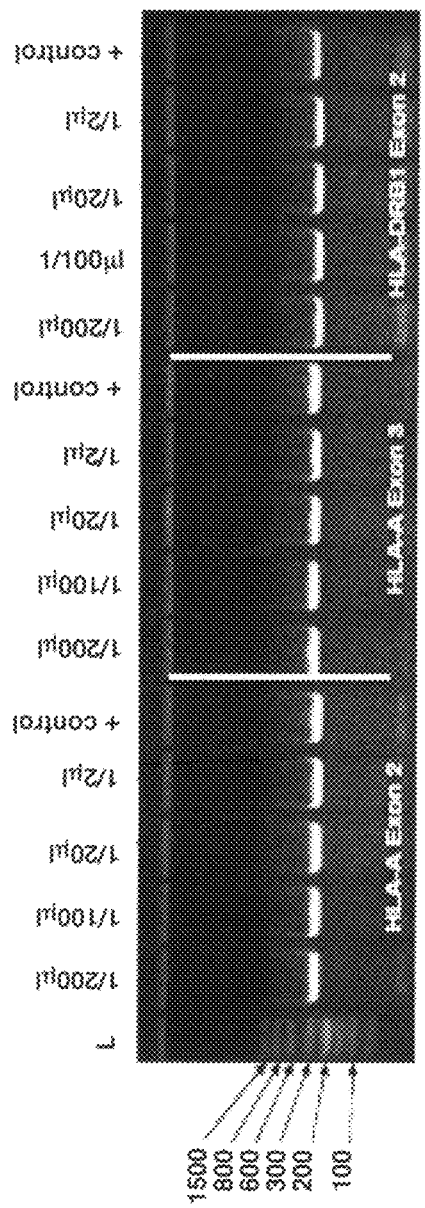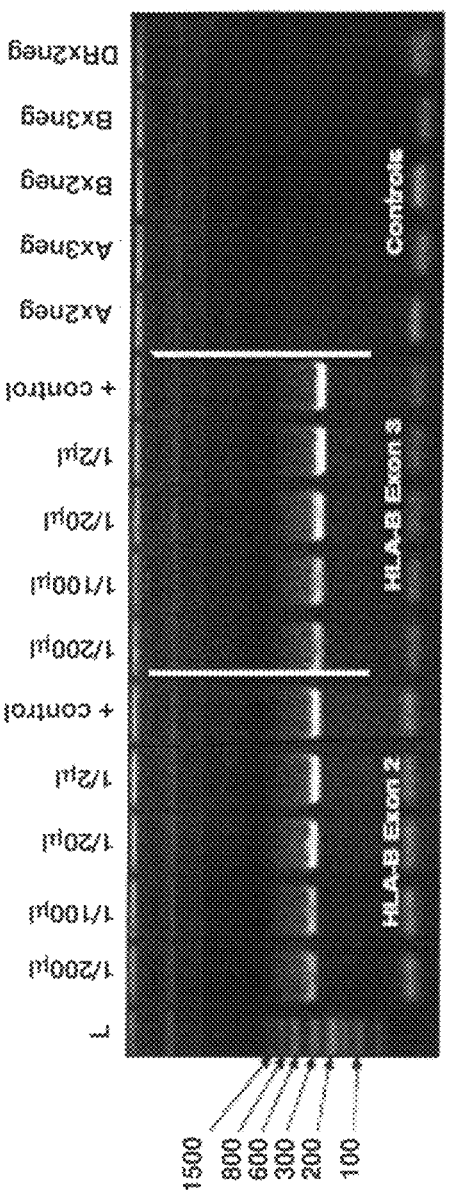
Fig. 1A
Fig. 1B

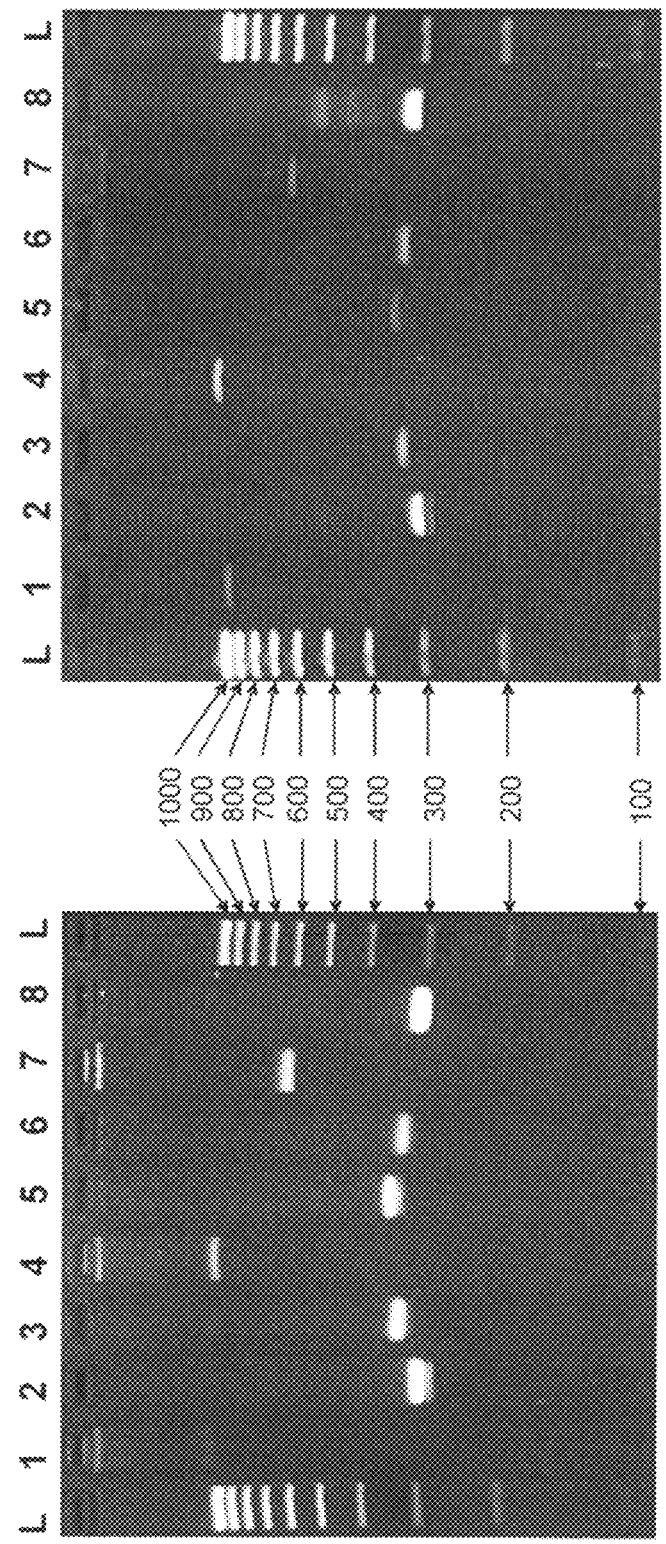

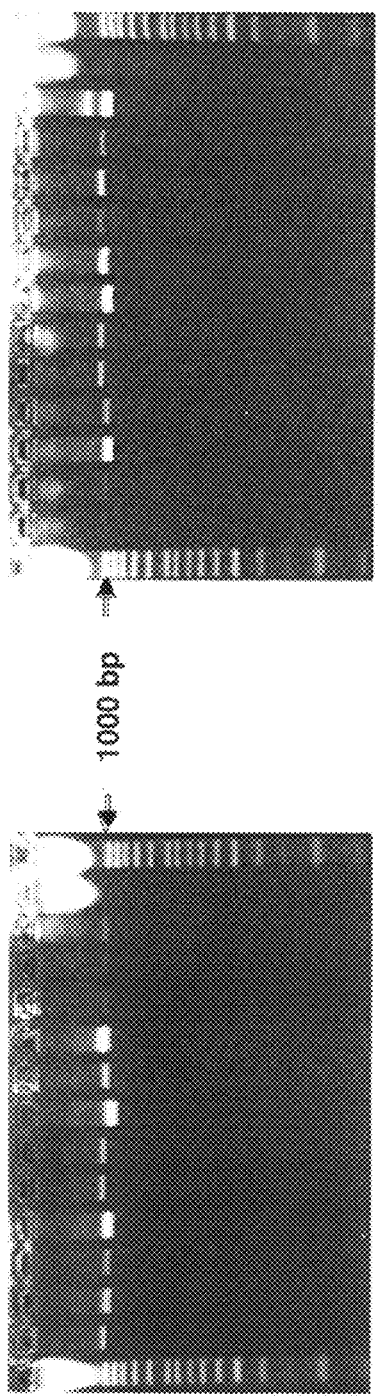
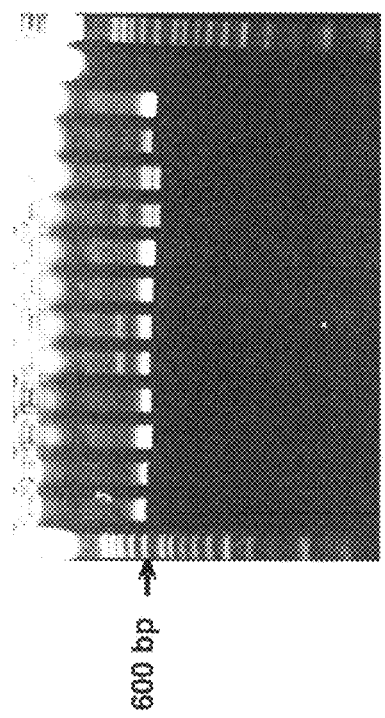
Fig. 3A
Fig. 3B
Fig. 3C
1000 bp
600 bp 300 bp

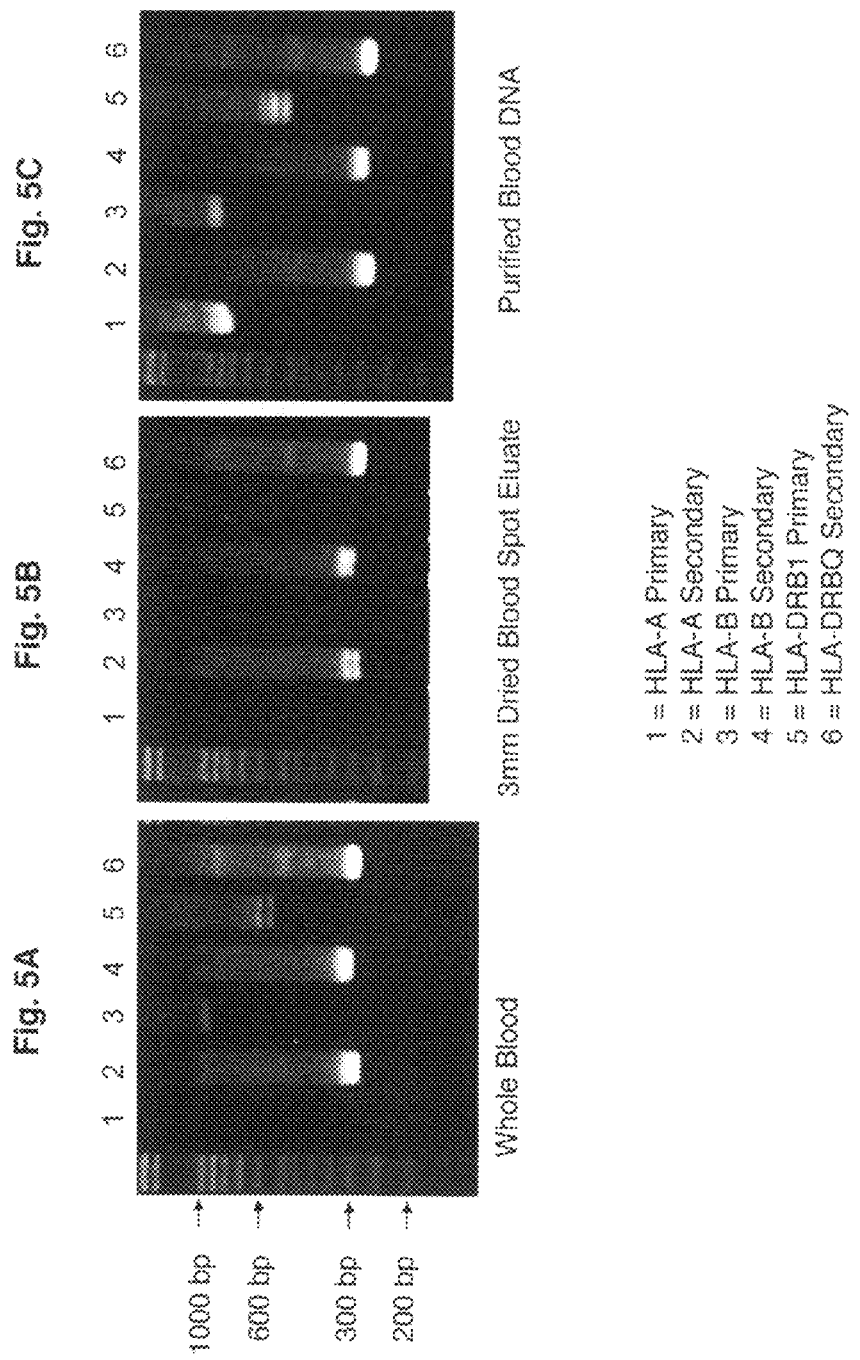

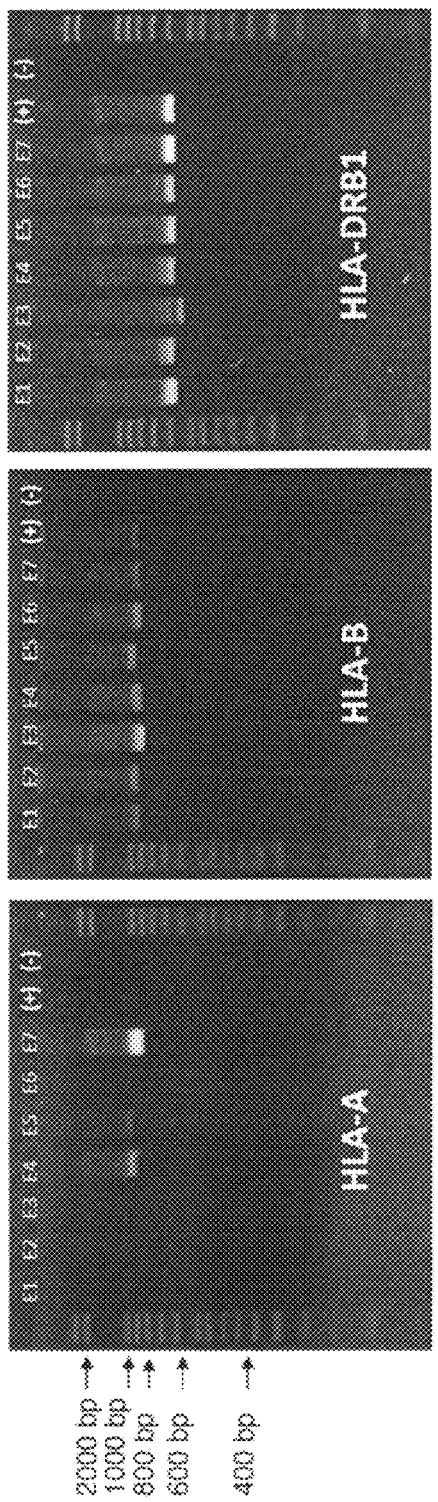
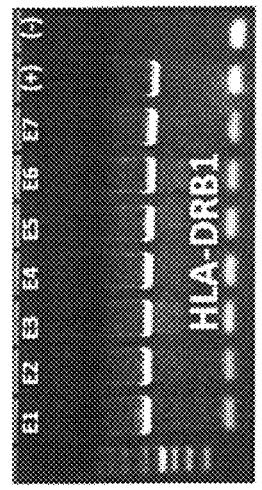
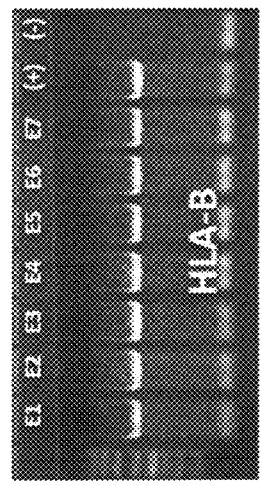
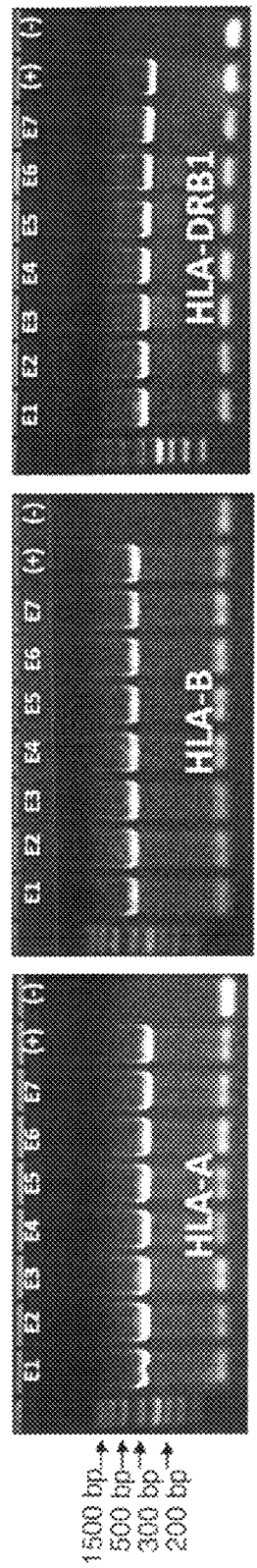
Fig. 5D  Fig. 5E  Fig. 5F  Fig. 5G  Fig. 5H  Fig. 5I

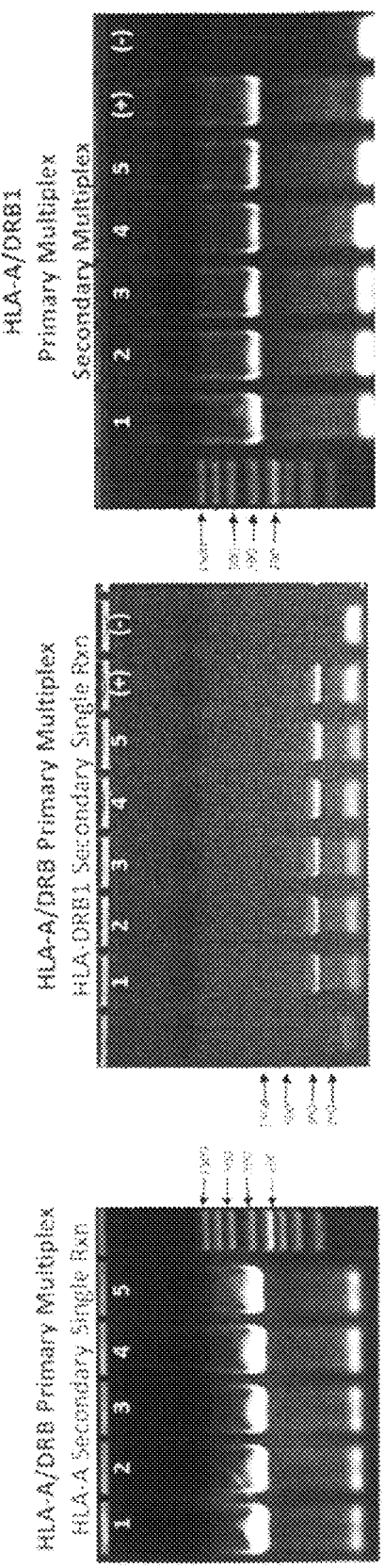

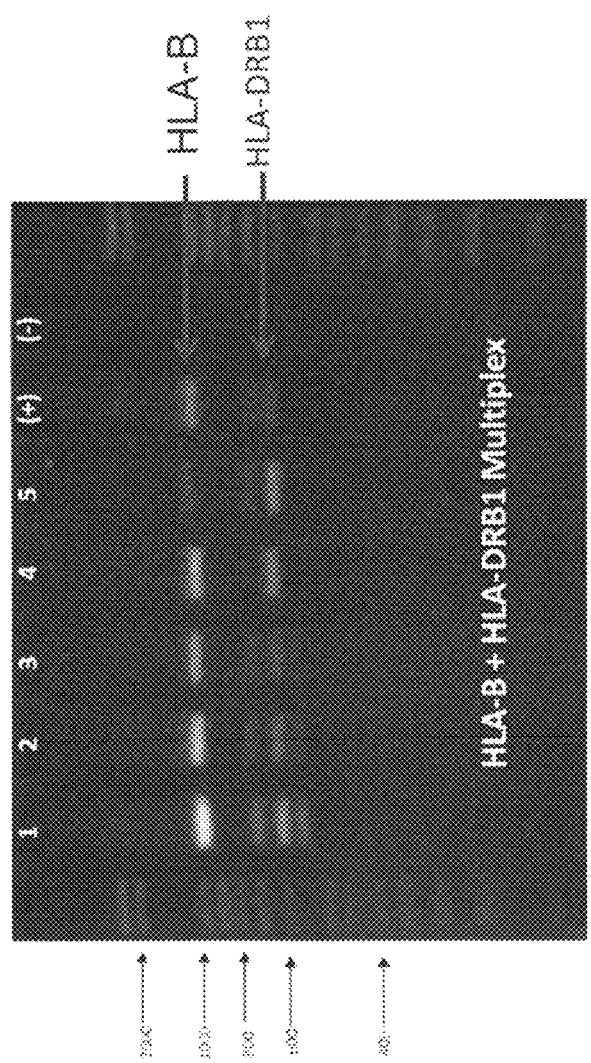

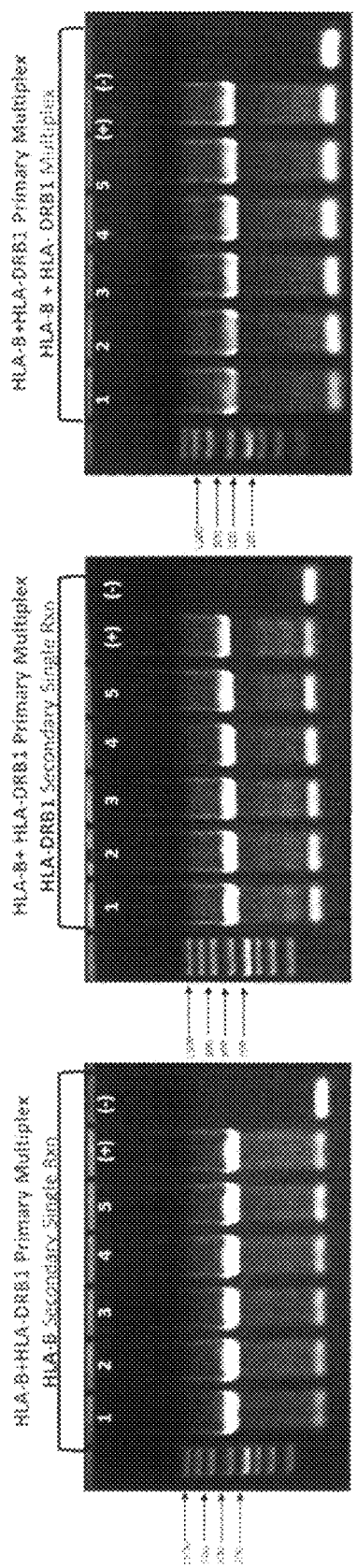

SEQUENCE LISTING

<160> NUMBER OF SEQ ID NOS: 27

<210> SEQ ID NO 1
<211> LENGTH: 20
<212> TYPE: DNA
<213> ORGANISM: Artificial sequence
<220> FEATURE:
<223> OTHER INFORMATION: forward HLA-A locus primary primer 1

<400> SEQUENCE: 1
gcctctgygg ggagaagcaa                                               20

<210> SEQ ID NO 2
<211> LENGTH: 22
<212> TYPE: DNA
<213> ORGANISM: Artificial sequence
<220> FEATURE:
<223> OTHER INFORMATION: reverse HLA-A locus primary primer 1

<400> SEQUENCE: 2
gtcccaattg tctcccctcc tt                                            22

<210> SEQ ID NO 3
<211> LENGTH: 22
<212> TYPE: DNA
<213> ORGANISM: Artificial sequence
<220> FEATURE:
<223> OTHER INFORMATION: forward HLA-B locus primary primer 2a

<400> SEQUENCE: 3
gggaggagcg aggggaccgc ag                                            22

<210> SEQ ID NO 4
<211> LENGTH: 22
<212> TYPE: DNA
<213> ORGANISM: Artificial sequence
<220> FEATURE:
<223> OTHER INFORMATION: forward HLA-B locus primary primer 2b

<400> SEQUENCE: 4
gggaggagag aggggaccgc ag                                            22

<210> SEQ ID NO 5
<211> LENGTH: 22
<212> TYPE: DNA
<213> ORGANISM: Artificial sequence
<220> FEATURE:
<223> OTHER INFORMATION: forward HLA-B locus primary primer 2c

<400> SEQUENCE: 5
gggaggagca aggggaccgc ag                                            22

<210> SEQ ID NO 6
<211> LENGTH: 23
<212> TYPE: DNA

```
<213> ORGANISM: Artificial sequence
<220> FEATURE:
<223> OTHER INFORMATION: reverse HLA-B locus primary primer 1

<400> SEQUENCE: 6
ggaggccatc ccgggcgatc tat                                        23

<210> SEQ ID NO 7
<211> LENGTH: 23
<212> TYPE: DNA
<213> ORGANISM: Artificial sequence
<220> FEATURE:
<223> OTHER INFORMATION: reverse HLA-B locus primary primer 3

<400> SEQUENCE: 7
ggaggccatc cccggcgacc tat                                        23

<210> SEQ ID NO 8
<211> LENGTH: 24
<212> TYPE: DNA
<213> ORGANISM: Artificial sequence
<220> FEATURE:
<223> OTHER INFORMATION: reverse HLA-B locus primary primer 3a

<400> SEQUENCE: 8
ttctccattc aacggagggc gaca                                       24

<210> SEQ ID NO 9
<211> LENGTH: 24
<212> TYPE: DNA
<213> ORGANISM: Artificial sequence
<220> FEATURE:
<223> OTHER INFORMATION: reverse HLA-A locus primary primer 3c

<400> SEQUENCE: 9
ttctccattc aagggagggc gaca                                       24

<210> SEQ ID NO 10
<211> LENGTH: 21
<212> TYPE: DNA
<213> ORGANISM: Artificial sequence
<220> FEATURE:
<223> OTHER INFORMATION: forward HLA-DRB1 locus primary primer 1a

<400> SEQUENCE: 10
cttggaggtc tccagaacag g                                          21

<210> SEQ ID NO 11
<211> LENGTH: 21
<212> TYPE: DNA
<213> ORGANISM: Artificial sequence
<220> FEATURE:
<223> OTHER INFORMATION: forward HLA-DRB1 locus primary primer 1b

<400> SEQUENCE: 11
cttagaggtc tccagaaccg g                                          21

<210> SEQ ID NO 12
<211> LENGTH: 25
<212> TYPE: DNA
<213> ORGANISM: Artificial sequence
<220> FEATURE:
<223> OTHER INFORMATION: reverse HLA-DRB1 locus primary primer 4-xx

<400> SEQUENCE: 12
cacacacaca cacacactca gattc                                      25
```

<210> SEQ ID NO 13
<211> LENGTH: 25
<212> TYPE: DNA
<213> ORGANISM: Artificial sequence
<220> FEATURE:
<223> OTHER INFORMATION: reverse HLA-DRB1 locus primary primer 4-07

<400> SEQUENCE: 13
cacacacaca accacactca gattc                                           25

<210> SEQ ID NO 14
<211> LENGTH: 25
<212> TYPE: DNA
<213> ORGANISM: Artificial sequence
<220> FEATURE:
<223> OTHER INFORMATION: reverse HLA-DRB1 locus primary primer 4-10

<400> SEQUENCE: 14
cacacacaca cacagagtca gattc                                           25

<210> SEQ ID NO 15
<211> LENGTH: 29
<212> TYPE: DNA
<213> ORGANISM: Artificial sequence
<220> FEATURE:
<223> OTHER INFORMATION: forward HLA-A exon 2 secondary primer 2b-24

<400> SEQUENCE: 15
agcctggttc actsctcgyc cccaggctc                                       29

<210> SEQ ID NO 16
<211> LENGTH: 33
<212> TYPE: DNA
<213> ORGANISM: Artificial sequence
<220> FEATURE:
<223> OTHER INFORMATION: reverse HLA-A exon 2 secondary primer 2a-28

<400> SEQUENCE: 16
tactacaacc ttgcccgctc tggttgtagt agc                                  33

<210> SEQ ID NO 17
<211> LENGTH: 30
<212> TYPE: DNA
<213> ORGANISM: Artificial sequence
<220> FEATURE:
<223> OTHER INFORMATION: forward HLA-A exon 3 secondary primer 2b-24

<400> SEQUENCE: 17
gtgagaacta gtcsgggcca ggttctcaca                                      30

<210> SEQ ID NO 18
<211> LENGTH: 28
<212> TYPE: DNA
<213> ORGANISM: Artificial sequence
<220> FEATURE:
<223> OTHER INFORMATION: reverse HLA-A exon 3 secondary primer 2b-26

<400> SEQUENCE: 18
gtaccaggtt cccgtggccc cyggtacc                                        28

<210> SEQ ID NO 19
<211> LENGTH: 30
<212> TYPE: DNA
<213> ORGANISM: Artificial sequence
<220> FEATURE:

<223> OTHER INFORMATION: forward HLA-B exon 2 secondary primer 2c-20

<400> SEQUENCE: 19
accctcttga gccgcgccgg kaggagggtc                                     30

<210> SEQ ID NO 20
<211> LENGTH: 34
<212> TYPE: DNA
<213> ORGANISM: Artificial sequence
<220> FEATURE:
<223> OTHER INFORMATION: reverse HLA-B exon 2 secondary primer 2a-28

<400> SEQUENCE: 20
tactacaacc ttgcctcgct ctggttgtag tagc                                34

<210> SEQ ID NO 21
<211> LENGTH: 29
<212> TYPE: DNA
<213> ORGANISM: Artificial sequence
<220> FEATURE:
<223> OTHER INFORMATION: forward HLA-B exon 3 secondary primer 2a-22

<400> SEQUENCE: 21
gtgagactta ccggggccag ggtctcaca                                      29

<210> SEQ ID NO 22
<211> LENGTH: 28
<212> TYPE: DNA
<213> ORGANISM: Artificial sequence
<220> FEATURE:
<223> OTHER INFORMATION: reverse HLA-B exon 3 secondary primer 2a-26

<400> SEQUENCE: 22
gtaccaggtt cccactgccc ctggtacc                                       28

<210> SEQ ID NO 23
<211> LENGTH: 33
<212> TYPE: DNA
<213> ORGANISM: Artificial sequence
<220> FEATURE:
<223> OTHER INFORMATION: forward DRB-1 exon 2 secondary primer 3-xx-24

<400> SEQUENCE: 23
aacgtgcttt tcgtgtccc cacagcacgt ttc                                  33

<210> SEQ ID NO 24
<211> LENGTH: 33
<212> TYPE: DNA
<213> ORGANISM: Artificial sequence
<220> FEATURE:
<223> OTHER INFORMATION: forward DRB-1 exon 2 secondary primer 3-04-24

<400> SEQUENCE: 24
aacgtgcttt tcttgtccc cccagcacgt ttc                                  33

<210> SEQ ID NO 25
<211> LENGTH: 33
<212> TYPE: DNA
<213> ORGANISM: Artificial sequence
<220> FEATURE:
<223> OTHER INFORMATION: forward DRB-1 exon 2 secondary primer 3-07-24

<400> SEQUENCE: 25
aacgtgcttt tttgtgcccc cacagcacgt ttc                                 33

```
<210> SEQ ID NO 26
<211> LENGTH: 28
<212> TYPE: DNA
<213> ORGANISM: Artificial sequence
<220> FEATURE:
<223> OTHER INFORMATION: reverse DRB-1 exon 2 secondary primer 3-xx-20

<400> SEQUENCE: 26
tgcagctttg ctcacctcgc cgctgcac                                          28

<210> SEQ ID NO 27
<211> LENGTH: 28
<212> TYPE: DNA
<213> ORGANISM: Artificial sequence
<220> FEATURE:
<223> OTHER INFORMATION: reverse DRB-1 exon 2 secondary primer 3-09-22

<400> SEQUENCE: 27
tgcagagttg cttacctcgc ctctgcac                                          28
```

METHODS FOR PCR AND HLA TYPING USING RAW BLOOD

CROSS-REFERENCE TO RELATED APPLICATIONS

This non-provisional application claims benefit of priority under 35 U.S.C. §119(e) of provisional application U.S. Ser. No. 61/281,404, filed Nov. 16, 2009, the entirety of which is hereby incorporated by reference.

BACKGROUND OF THE INVENTION

1. Field of the Invention

The present invention relates to the fields of PCR and HLA-typing. More specifically, the present invention discloses methods and systems for a tandem PCR process to amplify DNA or RNA within a raw biological specimen and subsequent HLA-typing thereof on an individual or population scale in a field or medical office environment.

2. Description of the Related Art

There is a new and rapidly growing understanding of the medical significance of HLA typing in current medicine. As an example Table 1 demonstrates the very large range of diagnostic and public health applications for HLA-typing.

TABLE I

|  | Clinical Correlation with Allele | Clinical Utility of HLA-B Screening |
|---|---|---|
| HLA-B Allele | | |
| B*07 | Ebola. Protective (with B*14). Non-fatal response to Ebola. | B*07 + B*14 are highly enriched in those who survive |
| B*0801 | Susceptibility to HIV-2 infection | HIV-2 screen for AIDS |
| B*11 | *Chlamydia trachomatis*. Protective against blindness from | Predictive of those who do not develop blindness |
| B*14 | Ebola. Protective (along with B*07). Non-fatal response to Ebola | B*07 and B*14 are highly enriched in those who survive. |
| B*1502 | Adverse Drug Response: carbamazepine-induced Stevens-Johnson in Chinese | FDA: All Chinese should be screened before Rx. |
| B*1503 | Poor AIDS prognosis after HIV-2 infection | HIV-2 screen for AIDS |
| B*17 | Leukemia in children. ALL high leukocyte counts at presentation. | B*17 and A*33 may combine to predict male relapse. |
| B*27 | Ankylosing Spondylitis (reactive arthritis): B*27 explains 50% of risk. | Severity of reactive arthritis strongly correlated with B*27. |
| B*27 | Reactive Arthritis: B*27 associated with enhanced risk of all forms of severe Reactive Arthritis. | Clinical B*27 Review in Nature. |
| B*27 | Crohn's Disease: HLA-B*27 appears to convey a very high risk of developing axial inflammation in Crohn's disease. | B*27 not associated with absolute Crohn's risk, but with subsequent inflammation. |
| B*27 | HIV-1: All B*27 alleles Protective, HIV-1 Elite Controller. | Also seems to correlate with early work on vaccines. |
| B*3503 | HIV-1: B*3501 is protective for HIV progression. Other B*35 alleles show rapid HIV progression. | As for B*57, a subtle change in B*35 allele has significant effects. |
| B*39 | Diabetes: Type I diabetes genetic risk explained by B*39 Plus HLA-DQB1 and HLA-DRB1. | Whole genome scanning study in Nature. |
| B*4402 | Cervical Cancer: Enhanced squamous cell cervical cancer RISK with one or more of A*0201-Cw*0501, DRB1*0401, or DQB1*0301. | HLA explains enhanced genetic risk for cervical cancer. B*4402 is the central theme. |
| B*51 | Behcet's disease: Autoimmune disease of the vasculature. | B*51 is strongly correlated with severity. |
| B*57 | HCV: Protective effect. | All B*57s correlated with spontaneous recovery. |
| B*5701 | Adverse drug response: Abacavir sensitivity. | Described as "Gold Standard: in 2009 for personalized medicine. |
| B*5701 | Adverse drug response: Abacavir sensitivity. | Large scale Australian screening trial confirms high predictive power for ADR. |
| B*5701 | HIV-1: Protective effect HIV-1 Elite Controller. Highest genetic correlation. HLA-C may be a secondary player. | The role of B*5701 in HIV risk on infection is the gold standard in host effects in infectious disease. |
| B*5702 | HIV-1: Not Protective HIV-1 Elite Controller | B*5701 and B*5702 must be cleanly resolved at high resolution for HIV progression and Abacvir ADR |
| B*5801 | Adverse drug response: Allopurinol sensitivity in Chinese. | Highly predictive of adverse response to allopurinol |
| Type II HLA Alleles | | |
| DRB1*0401 | Type 1 Diabetes (T1D) | Personalized T1D risk |
| DRB1*0401 | Multiple Sclerosis (MS) | Personalized MS risk |

TABLE I-continued

| | Clinical Correlation with Allele | Clinical Utility of HLA-B Screening |
|---|---|---|
| DRB1*0401 | Rheumatoid Arthritis (RA) | Personalized RA risk |
| DRB1*0402 | Type 1 Diabetes (T1D) | Personalized T1D risk |
| | Type 1 + Type II Allele Combinations | |
| B*4402, DRB1*1101 DQB1*0301 | High Risk for Cervical Cancer after HPV infection | Cervical Cancer screening test |
| | Type II allele combinations | |
| DQA1*0501: DQB1*0201 | T1D | Personalized T1D risk |
| DQA1*0501: DQB1*0201 | Celiac Disease | Key marker for celiac and other Autoimmune diseases |
| DQA1*0501: DQB1*0201 | T1D | Personalized T1D risk |
| DQA1*0501: DQB1*0201 | Celiac Disease | Key marker for celiac and other Autoimmune diseases |
| DRB1*0301: DQA1*0501: DQB1*0201 | Highest known inherited risk for T1D | Possible clinical and public health screening test for T1D |
| DRB1*04: DQA1*03: DQB1*0302 | Second Highest inherited risk for T1D | Possible clinical and public health screening test for T1D |
| DRB1*13 DQB1*06 | Predictive of resistance to AIDS upon HIV-1 infection | Possible clinical and public health screening test for AIDS |
| DRB1*15 DQB1*0602 | Correlated with high risk of cervical cancer After HPV infection | Possible cervical cancer screening test |
| | Important HLA allele combinations with Genes other than HLA | |
| (B*57, B*27) + KIR3DS1 | HLA-B*57 or B*27 types, which present Bw4-80I epitopes, paired with activating KIR type 3DS1, have highest power to predict resistance to AIDS, upon HIV-1 infection | Possible clinical and public health screening test for AIDS |
| HLA-Bw4 + KIR3DS1 | Poor survival prognosis for multiple myeloma | Possible diagnostic screening tool in cancer |

However, at present, HLA typing literally requires the effort of an entire molecular genetics laboratory. Incoming blood specimens must first be purified by methods such as spin columns or magnetic beads, followed by quantitation of the purified DNA by methods such as PicoGreen fluorimetry or UV absorbance. The quantified DNA is then subjected to PCR amplification and, following PCR, is then analyzed by high throughput re-sequencing or, more recently, by multiplex hybridization analysis by beads or by microarrays. Thus, the resulting workflow requires the effort of a full molecular genetics laboratory, and at least one full day to compile the final HLA-typing data. The complexity of such a standard workflow also introduces major concerns related to chain-of-custody and the requirement for complex and costly LIMS systems and workflow standard operating procedures, to keep track of sample flow through the several processing and analysis workstations.

Efforts to streamline the process have included obviating DNA purification. Previous attempts to perform PCR amplification from unpurified blood have been problematic even with the availability of variants of the Taq polymerase used for standard PCR. The use of raw blood as a PCR substrate has not yielded consistent results due to the extreme sample-to-sample variation in the white cell complement of blood and possible sample-to-sample variation in the very large excess of blood solutes which can interfere with the underlying PCR reaction.

Thus, there is a recognized need in the art for low equipment and consumable cost, high-throughput methods of gene amplification and HLA typing. Specifically, the present invention is deficient in a hands-free or automated, real-time high-resolution method of HLA typing without a need for first externally purifying the DNA from a sample. The present invention fulfills this long-standing need and desire in the art.

SUMMARY OF THE INVENTION

The present invention is directed to a method for amplifying a DNA of interest. The method comprises obtaining a raw sample comprising DNA, performing a first PCR on the raw sample to produce a first amplicon and diluting the first amplicon. A second PCR is performed thereon until all primers used in the second PCR reaction are consumed to produce a second amplicon, thereby amplifying the input sample DNA to a final amplified DNA product concentration that is limited by the primer concentration in the second PCR reaction, said second PCR reaction independent of the amount or purity of the DNA comprising the original sample.

The present invention is directed to a related invention where the first PCR is performed on a set of gene targets in parallel on the raw sample to produce the first set of amplicons and diluting the first set of amplicons. A second PCR is performed on the first set using the entire set of primary amplicon products as a set of templates for the second PCR reaction until all secondary PCR primers are consumed to produce a second amplicon set, thereby amplifying the DNA The present invention is directed to another related method further comprising labeling the second PCR primer pairs with one or more fluorophores.

The present invention is directed to yet another related method where the DNA comprises one or more genes of interest and the method further comprises hybridizing the second amplicon to probes having sequences of allele variations associated with the gene of interest, detecting a fluorescence pattern from the hybridized amplicon and assigning an allelotype based on the fluorescence pattern.

The present invention is directed to yet another related method further comprising sequencing the second amplicon for an analysis thereof.

The present invention also is directed to a method for amplifying one or more RNAs of interest. The method comprises obtaining a raw biological sample from an individual, performing a first reverse transcription PCR on the raw biological sample to produce a first cDNA amplicon(s) and diluting the first amplicon(s) and performing a second PCR thereon until all primers are consumed to produce a second amplicon(s), thereby amplifying the RNA(s) of interest.

The present invention is directed to a related method further comprising labeling the second PCR primer pairs with one or more fluorophores.

The present invention is directed to another related method further comprising hybridizing the second amplicon(s) to probes having sequences complementary to an area of interest in a gene sequence, detecting a fluorescence pattern from the hybridized amplicon and identifying one or more gene(s) or allelotype(s) thereof based on the fluorescence pattern.

The present invention is directed to yet another related method further comprising sequencing the second amplicon for an analysis thereof.

The present invention is directed further to a method for allelotyping a gene of interest. The method comprises obtaining a raw biological sample from one or more individuals, performing a first PCR on the raw biological sample using primers specific to the gene locus or a defined set of gene loci to produce a first amplicon or set of amplicons and then diluting the first amplicon or first set of amplicons and performing a second PCR with these amplicons serving as the template for the second PCR reaction using primers specific to an exon or a set of exons within the gene locus until all primers are consumed to produce an amplicon set from the second PCR reaction. The second amplicon set is hybridized to probes having sequences of allele variations associated with the gene or gene set of interest, a signal is detected from the hybridized amplicon set and allelotype(s) are assigned based on the detected hybridization signals.

Other and further objects, features, and advantages will be apparent from the following description of the presently preferred embodiments of the invention, which are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIGS. 1A-1B are gels showing that, beginning with 10 ng of purified DNA, the amount of final Secondary PCR amplicon product is constant over a range of Primary PCR amplicon concentrations used as template for the Secondary PCR amplification: for the HLA-A exon set 2 or 3 and HLA-DRB1 exon 2 (FIG. 1A) and the HLA-B exon set 2 or 3 (FIG. 1B).

FIGS. 2A-2B are gels showing Primary and Secondary HLA-A, HLA-B, and DRB1 PCR Amplicons generated from 2 μl of whole fluid blood (FIG. 2A) or 10 ng of purified human genomic DNA (FIG. 2B). Resolved on 2% Agarose SFR gel electrophoresis (Amresco 1×TBE gel). #1: HLA-A locus specific Primary PCR product (approx. 1,000 bp); #2: HLA-A exon 2 Secondary PCR Product (approx. 300 bp); #3: HLA-A exon 3 Secondary PCR Product (approx. 320 bp); #4: HLA-B locus specific Primary PCR product (approx. 1,000 bp); #5: HLA-B exon 2 Secondary PCR Product (approx. 320 bp); #6: HLA-B exon 3 Primary PCR product (approx. 310 bp); #7: DRB1 locus specific Primary PCR product (approx. 650 bp); #8: DRB1 exon 2 Secondary PCR Product (approx. 310 bp); L: Bio-Rad EZ Load ladder.

FIGS. 3A-3C are gels showing locus specific Primary PCR products generated from 12 un-purified whole blood templates for HLA-A (FIG. 3A), HLA-B (FIG. 3B), and HLA-DRB1 (FIG. 3C).

FIG. 5A-5C are gels showing HLA-A, HLA-B, and DRB1 PCR Primary PCR products then Secondary PCR Amplicon sets generated from 1 μl whole fluid blood (left) compared to the same reactions performed fluid derived by re-hydration of a 3 mm dried blood spot (middle) that had been re-hydrated as described in the protocol of Example 5, and the same reaction performed on 10 ng of purified DNA from the same blood specimen (right). FIGS. 5D-5F display the primary PCR reactions specific for HLA-A, HLA-B & HLA-DRB1 for these 8 unique raw blood samples obtained from anonymized volunteers, while FIGS. 5G-5I display the secondary PCR reactions specific for HLA-A, HLA-B & HLA-DRB1 for the same 8 raw blood samples. As can be seen, although the yield of primary PCR product is highly variable among the set of 8 raw blood samples (FIGS. 5D-5F) the subsequent secondary PCR reaction has generated a series of amplified exons which are nearly identical in yield and specificity, among the set of 8 raw blood specimens (FIGS. 5G-5I). Gels were resolved on 2% Agarose SFR (Amresco), 1×TBE gel. L: Bio-Rad EZ Load ladder. For both HLA-A and HLA-B, the secondary PCR product observed on the gel is an unresolved pair of bands, derived from multiplex (n=2) amplification of exon2 & exon3 in the same PCR reaction.

FIGS. 6B-6G display the product of the tandem PCR reactions performed on raw cheek swabs from a total of 12 donors. FIGS. 6B-6D display the primary PCR reactions specific for HLA-A, HLA-B & HLA-DRB1 for these 12 raw buccal swab samples, while FIGS. 6E-6G display the secondary PCR reactions specific for HLA-A, HLA-B & HLA-DRB1 for the sample 12 raw buccal swab samples. As can be seen, although the yield of primary PCR product is highly variable among the set of 12 raw, re-hydrated buccal swabs samples (FIGS. 6B-6D) the subsequent secondary PCR reaction has generated a series of amplified exons which are nearly identical in yield and specificity, among the set of 12 raw buccal swab specimens (FIGS. 6E-6G).

FIGS. 7A-7F show Tandem PCR amplification of multiple HLA genes in parallel: HLA-A & HLA-DRB1. Locus-specific multiplex and exon specific multiplex HLA-PCR reactions were performed on a set of 5 samples retrieved from the UCLA Immunogenetics reference panel for HLA Class I. FIG. 7A diagrams the primary HLA-PCR where the locus-specific primers for the genes HLA-A and HLA-DRB1 were used to multiplex the primary PCR. A 1:100 dilution was performed on the product of the locus-specific PCR and 2_I of the dilution were used in a set of secondary nested PCR that targets HLA-A exons 2 and 3 and for HLA-DRB1 exon 2. The first nested secondary PCR reaction amplified only HLA-A exons 2 and 3. A second PCR reaction was performed independently on the product of the primary multiplex PCR where only HLA-DRB1 exon 2 was amplified. The third independent secondary PCR reaction used the mentioned template from the primary multiplex reaction and amplified in multiplex format the exons 2 and 3 for HLA-A and exon 2 for HLA-DRB1. FIG. 7B displays the primary PCR reactions specific for HLA-A and HLA-DRB1 where the two genes were amplified simultaneously for 5 samples of 10 ng of human genomic purified DNA. Two different size bands are resolved in the gel corresponding to HLA-A at 1000 bp and HLA-DRB1 at approximately 650 bp. FIGS. 7C-7E display the secondary multiplex reactions performed after the first multiplex PCR of HLA-A plus HLA-DRB1 took place. FIG. 7C shows the exon-specific HLA-PCR for HLA-A exons 2 and 3. FIG. 7D displays the exon-specific HLA-PCR for HLA-DRB1 exons 2. Finally, FIG. 7E displays the amplification in parallel of HLA-A exons 2 and 3, and HLA-DRB1 exon 2 in the same exon specific HLA-PCR. The bands cannot be differentiated in the gel due to the similarity of amplicon size. The fragment size for HLA-A exons 2 and 3 is approximately 320 bp while HLA-DRB1 exon 2 is 310 bp long. Gels were resolved using 2% agarose gels, and visualized using Amresco EZ-Vision DNA Dye FIG. 7F displays genotyping data of 2 samples chosen from the UCLA Immunogenetics reference panel with known genotypes as disclosed on column labeled as UCLA. The green color on the tables corresponds to 100% match genotypes. The blue color represents genotyping data from GUSA matching at the serological level. White cells represents mismatched genotypes or false positive hybridization subjected to adjustment of thresholds in analysis software.

FIGS. 7G-7L show tandem PCR amplification of multiple HLA genes in parallel: HLA-A & HLA-DRB1. Locus-specific multiplex and exon specific multiplex HLA-PCR reactions were performed on a set of 5 samples retrieved from the UCLA Immunogenetics reference panel for HLA Class I. FIG. 7G diagrams the primary HLA-PCR where the locus-specific primers for the genes HLA-B and HLA-DRB1 were used to multiplex the primary PCR. A 1:100 dilution was performed on the product of the locus-specific PCR and 2_I of the dilution were used in a set of secondary nested PCR that targets HLA-B exons 2 and 3 and for HLA-DRB1 exon 2. The first nested secondary PCR reaction amplified only HLA-B exons 2 and 3. A second PCR reaction was performed independently on the product of the primary multiplex PCR where only HLA-DRB1 exon 2 was amplified. The third independent secondary PCR reaction used the mentioned template from the primary multiplex reaction and amplified in multiplex format the exons 2 and 3 for HLA-B and exon 2 for HLA-DRB1. FIG. 7H displays the primary PCR reactions specific for HLA-B and HLA-DRB1 where the two genes were amplified simultaneously for 5 samples of 10 ng of human genomic purified DNA. Two different size bands are resolved in the gel corresponding to HLA-B at 1000 bp and HLA-DRB1 at approximately 650 bp. FIGS. 7I-7K display the secondary multiplex reactions performed after the first multiplex PCR of HLA-B plus HLA-DRB1 took place. FIG. 7I shows the exon-specific HLA-PCR for HLA-B exons 2 and 3. FIG. 7J displays the exon-specific HLA-PCR for HLA-DRB1 exons 2. Finally, FIG. 7K displays the amplification in parallel of HLA-B exons 2 and 3, and HLA-DRB1 exon 2 in the same exon specific HLA-PCR. The bands cannot be differentiated in the gel due to the similarity of amplicon size. The fragment size for HLA-B exons 2 and 3 is approximately 320 bp while HLA-DRB1 exon 2 is 310 bp long. Gels were resolved using 2% agarose gels, and visualized using Amresco EZ-Vision DNA Dye FIG. 7L displays genotyping data of 2 samples chosen from the UCLA Immunogenetics reference panel with known genotypes as disclosed on column labeled as UCLA. The green color on the tables corresponds to 100% match genotypes. The blue color represents genotyping data from Genomics USA matching at the serological level. White cells in the table represent mismatched genotypes or false positive hybridization subjected to adjustment of thresholds in analysis software.

Figure 8A:
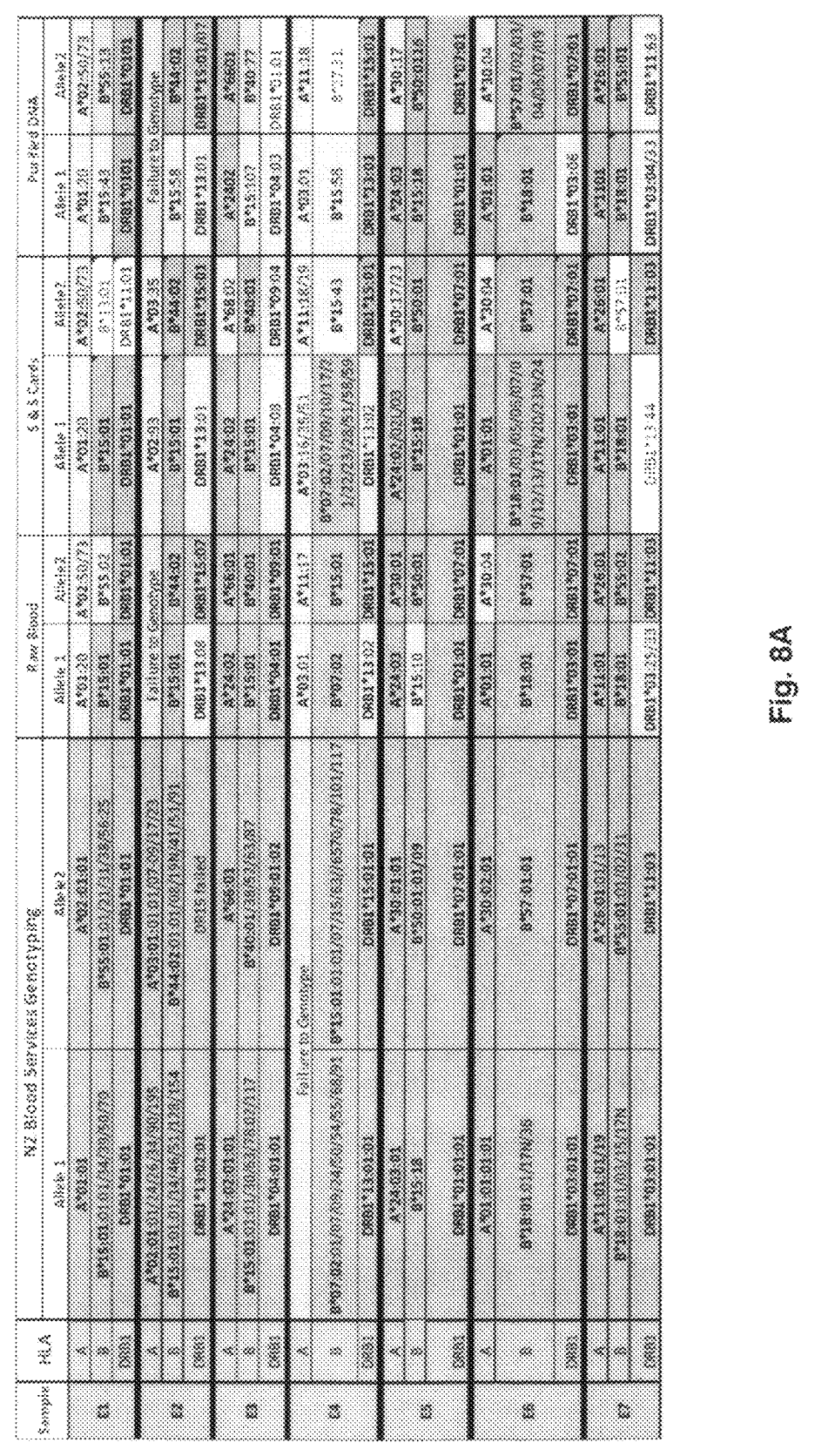
Figure 8B:
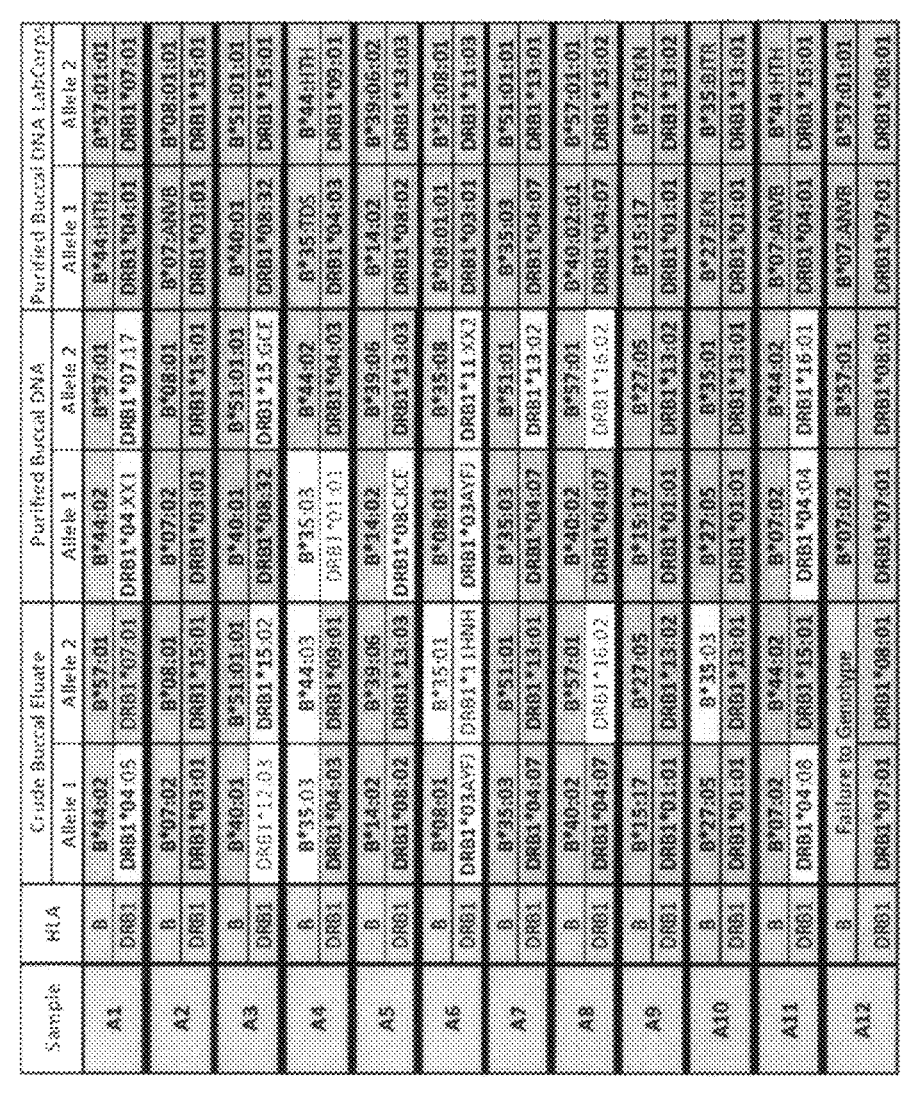

FIGS. 8A-8B are Tables showing HLA-typing obtained via microarray analysis for raw blood, dried blood spots (7A) and for raw buccal swabs and the corresponding DNA purified from those swabs (7B) obtained via the methods of Examples 5&6. Genotyping data obtained by analysis of raw blood, re-hydrated blood spots, and purified DNA of seven different blood samples collected in EDTA as the anticoagulant of choice was compared to genotyping data provided by New Zealand Blood Services for validation. The data shows overall agreement between results at serological level in most instances and high resolution in the remaining samples (FIG. 8A). FIG. 8B displays genotyping data of crude buccal sample eluate compared to the matching purified DNA and independent genotyping provided by Lab Corps. The data demonstrate a high level of agreement of the 11 samples collected locally. Green color demonstrate 100% agreement between Genomics USA genotyping and Lab Corps. The blue shaded data points represent agreement at the serological level, while white data points refer to failure to match the genotypes provided by the third party.

DETAILED DESCRIPTION OF THE INVENTION

Figure 4A:
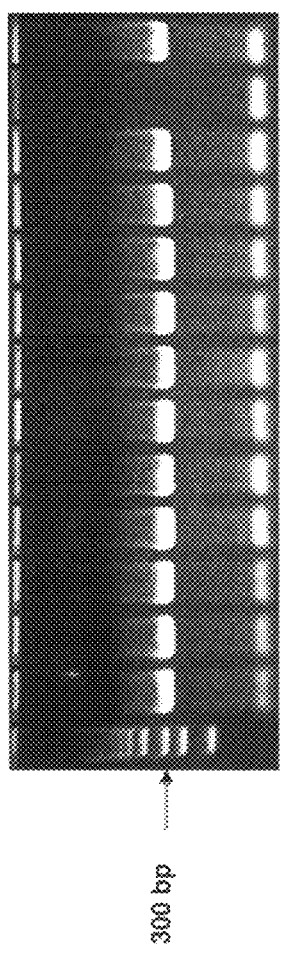
FIGS. 4A-4C are gels showing exon specific Secondary PCR reactions performed upon the Primary PCR reaction products displayed in FIG. 3: using a set of PCR primers specific for HLA-A exon set 2 and 3, performed simultaneously as a multiplex PCR reaction (FIG. 4A), using a set of PCR primers specific for HLA-B exons 2 and 3, performed simultaneously as a multiplex PCR reaction (FIG. 4B), and using a set of PCR primers specific for all related variants of HLA-DRB1 exon 2, performed simultaneously as a multiplex PCR reaction (FIG. 4C). Template for these Secondary PCR reactions was the locus specific Primary PCR product, amplified directly from 12 whole blood samples shown in FIGS. 3A-3C, diluted 1:100 in molecular biology grade water then applied as 24 each into the 50 μL Secondary PCR reactions listed above. Negative control is also shown.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the terms "individual" or "population" refers to donors or potential donors of the biological specimen, for example, raw blood, used in the amplification and HLA-typing methods described herein.

As used herein, the terms "raw sample" or "raw biological sample" refer to an unprocessed or unpurified sample, with the exception of those steps required to rehydrate the raw sample if it is or has been dried, that is used for a first amplification as described herein.

In one embodiment of the present invention there is provided a method for amplifying a DNA of interest, comprising obtaining a raw sample comprising DNA; performing a first PCR on the raw sample to produce a first amplicon; diluting the first amplicon; and performing a second PCR thereon until all primers used in the second PCR reaction are consumed to produce a second amplicon, thereby amplifying the input sample DNA to a final amplified DNA product concentration that is limited by the primer concentration in the second PCR reaction, said second PCR reaction independent of the amount or purity of the DNA comprising the original sample.

Further to this embodiment the method may comprise labeling the second PCR primer with one or more fluorophores. An example of a fluorophore is a cyanine dye. In another further embodiment the method may comprise sequencing the second amplicon for an analysis thereof. In this further embodiment analysis may determine one or more of identity, paternity of an individual, forensic information, tissue matching, risk factors for the development of disease, or response to medication.

In one aspect of all embodiments the method may comprise performing the first PCR on a set of gene targets in parallel on the raw sample to produce a first set of amplicons; diluting the first set of amplicons; and performing a second PCR thereon, using the entire set of primary amplicon products as a set of templates for the second PCR reaction until all secondary PCR primers are consumed to produce a second amplicon set, thereby amplifying the DNA. In this aspect less than 5 gene targets, less than 10 gene targets or less than 20 gene targets may be amplified in parallel. Also, the gene targets may be HLA-DRB1, DQ-A1 and DQB1. may be DQ-A1 and DQ-B1 or may be HLA-B and KIR. Also, the gene targets are two hypervariable regions near the mitochondrial origin of replication and one or more additional mitochondrial genes. In addition the gene targets may be segments of microbe-specific microbial 16S DNA genes such that the method detects microbes in the raw samples.

In another aspect of all embodiments the DNA comprises one or more genes of interest and the method may further comprise hybridizing the second amplicon to probes having sequences of allele variations associated with the gene of interest; detecting a fluorescence pattern from the hybridized amplicon; and assigning an allelotype based on the fluorescence pattern. The gene(s) of interest may be an HLA-A gene, an HLA-B gene, an HLA-DRB1 gene, an HLA-DQA1 gene, or an HLA-DQB1 gene.

In all embodiments the primers for the first PCR may be locus-specific primers. Examples of locus-specific primers may have sequences shown in SEQ ID NOS: 1-14. Also, in all embodiments the primers for the second PCR reaction target DNA sequences may be contained within the amplified product of the first PCR reaction. In one aspect, the primers for the second PCR reaction may be a set of multiple exon-specific primers. Particularly, exon-specific primers may have sequences shown in SEQ ID NOS: 15-27. Furthermore, the raw sample may be fresh or rehydrated and comprises unprocessed fluid blood, dried unprocessed blood, a fresh buccal swab sample, a dried buccal swab sample, fecal material, a vaginal sample or a sample obtained by swabbing an animate or inanimate surface or object. Further still in all embodiments the DNA may be mitochondrial DNA.

In another embodiment of the present invention there is provided a method for amplifying one or more RNAs of interest, comprising obtaining a raw biological sample from an individual; performing a first reverse transcription PCR on the raw biological sample to produce a first cDNA amplicon(s); diluting the first amplicon(s) and performing a second PCR thereon until all primers are consumed to produce a second amplicon(s), thereby amplifying the RNA(s) of interest.

Further to this embodiment the method comprises labeling the second PCR primers with one or more fluorophores. An example of a fluorophore is a cyanine dye. In both embodiments the raw biological sample may be fresh or rehydrated and comprises blood, a buccal sample, or a vaginal sample or other sample obtained by swabbing an animate surface or object.

In one aspect of this further embodiment the method may comprise hybridizing the second amplicon or set of amplicons to probes having sequences complementary to an area of interest in a gene sequence; detecting a fluorescence pattern from the hybridized amplicon; and identifying one or more genes or allelotypes thereof based on the fluorescence pattern. Examples of a gene are one or more of an HLA-A gene, an HLA-B gene, an HLA-DRB1 gene, an HLA DQA1 gene, an HLA DQB1 gene or a KIR gene. In another aspect of these embodiments the method may further comprise sequencing the second amplicon(s) for an analysis thereof. In this aspect analysis may determine one or more of identity, paternity of an individual, forensic information, tissue matching, risk factors for the development of disease, or response to medication.

In all embodiments the second PCR may be linear PCR and the second amplicon(s) are cRNA(s). Alternatively, the second PCR may be real time PCR and the primers are exon specific to the first cDNA amplicon(s). In addition, the first amplicon(s) are one or more of an HLA-A, an HLA-B or an HLA-DBR1, an HLA-DQA1, or an HLA-DQ-B1 cDNA(s)

and the exon-specific primers have a sequence shown in SEQ ID NOS: 15-27 Furthermore the raw sample may be as described supra.

In yet another embodiment of the present invention there is provided a method for allelotyping a gene of interest, comprising obtaining a raw biological sample from one or more individuals; performing a first PCR on the raw biological sample using primers specific to the gene locus or a defined set of gene loci to produce a first amplicon or first set of amplicons; diluting the first amplicon or first set of amplicons and performing a second PCR with the amplicon(s) serving as the template for the second PCR reaction using primers specific to an exon or a set of exons within the gene locus until all primers are consumed to produce an amplicon set from the second PCR reaction; hybridizing the second amplicon or amplicon set to probes having sequences of allele variations associated with the gene or gene set of interest; detecting a signal from the hybridized amplicon or amplicon set; and assigning an allelotype based on the detected hybridization signal. In an aspect of this embodiment the first amplicon or amplicon set may be cDNA amplified from RNA comprising the sample and the second PCR is linear PCR or real time PCR performed thereon.

In this embodiment the detectable signal may be fluorescence where the second PCR primer pairs are labeled with one or more fluorophores. An example of a fluorophore is a cyanine dye. Also, the first and second PCR primer sequences, the gene of interest and the raw biological sample may be as described supra. In addition the individuals may comprise a population in a field environment.

Provided herein are methods and systems for individual or population-scale amplification and HLA-typing of DNA or RNA using a raw specimen. For example, although not limited to, microfabricated devices or "Lab-on-a-Chip" (LoC) devices provide high value, clinically relevant applications in diagnostics or public health. Implementing the instant methods and systems enables a rapid, miniaturized point-of-collection analysis of DNA or RNA that significantly lowers costs in equipment and consumables. Particularly, the methods and systems provided herein allow the user to completely bypass DNA purification and subsequent DNA quantitation prior to HLA-typing.

Thus, the present invention provides a method of DNA or RNA amplification from a raw biological specimen. The specimen may be, but not limited to, blood, such as is obtained from a finger prick on one or more individuals or heel prick on neonates and older infants. The specimen may be used immediately in droplet form for amplification or dried onto a card, e.g., a Guthrie card, for subsequent re-hydration, followed by amplification or other processing. The methods for obtaining a blood sample or drop, as well as drying, storing and rehydrating a blood drop, are well-known and standard in the art. The quantity of raw blood or rehydrated dried blood useful for amplification is about 1-2 microliters. The raw blood samples may be collected from a single individual or from a population. Collection of samples may be performed in the field, at a diagnostic laboratory or in a clinic or doctor's office. Amplification of DNA and subsequent HLA-typing using the amplicon may be performed in real-time at the point of collection.

The specimen may also be, but not limited to, epithelial cells, such as is obtained from a cheek swab with a Q-tip on one or more adults or neonates or older infants. The specimen may be used immediately as a wet swab for amplification or air-dried for subsequent re-hydration, followed by amplification or other processing. The methods for obtaining a swab sample, as well as drying, storing and rehydrating a swab sample are well-known and standard in the art. The quantity of raw moist swab material or rehydrated dried swab material useful for amplification is about 1-2 microliters. The raw swab samples may be collected from a single individual or from a population. Collection of samples may be performed in the field, at a diagnostic laboratory or in a clinic or doctor's office. Amplification of DNA and subsequent HLA-typing using the amplicon may be performed in real-time at the point of collection or upon shipping to a regional laboratory.

PCR amplification of DNA is performed on the collected raw specimen without having to first purify the DNA: using highly gene- or locus-specific primers, as is currently done via well-known and standard methods. Examples of locus specific primers have the sequences shown in SEQ ID NOS: 1-14. Tandem PCRs (PCR #1, the PCR #2) are run such that the first PCR reaction occurs on the raw specimen, such as blood, or rehydrated dried blood spots, rehydrated raw swab eluate or a fecal sample. It is known that because of uncontrolled contamination of the specimen with PCR inhibitors in the blood or swab material, the yield of the primary PCR reaction can vary significantly. This has been responsible for the general failure of such raw blood or raw swab PCR in a commercial setting.

However, in the present invention, the second PCR reaction occurs using the product of the first PCR reaction with a subset or sub-sequence of locus-specific primers, such as, but not limited to, exon-specific primers. Examples of exon specific primers have the sequences shown in SEQ ID NOS: 15-27. Because the second PCR reaction is set up to be primer-limited, that is, the second PCR reaction intentionally proceeds until all added PCR primer oligonucleotides are consumed, the amount of PCR product derived from the second PCR reaction becomes independent of the variable amount of product obtained in the first PCR reaction. Consequently, the significant variation in the yield of the first PCR reaction due to uncontrolled contamination from within the raw blood specimen, is corrected by the self-limiting nature of the second reaction. Moreover, the product of the first PCR reaction is significantly diluted into the second PCR reaction, thus minimizing the effect of PCR inhibitors that had contaminated the raw specimen at the outset. The net result is a predetermined amount of final PCR product always being obtained via the use of this series of two PCR reactions, i.e., the amount of final product always will be determined by the amount of PCR primer used in the second of the two PCR reactions. Moreover, via significant dilution of the primary PCR reaction into the second PCR reaction, the overall tandem PCR reaction is thus substantially independent of uncontrolled variations in PCR inhibitor contamination within the original raw sample.

RNA amplification may be accomplished using the tandem PCR methods described herein. As with DNA amplification, a raw blood sample, either fresh or a rehydrated dry sample is obtained and a reverse transcription (RT) PCR is performed followed by PCR, e.g., real time PCR, endpoint PCR or linear cRNA amplification or synthesis.

The amplicon, which may be, but not limited to, an amplified human leukocyte antigen gene HLA-A, HLA-B or HLA-DRB1 or DQA1 or DQB1 gene or the HLA receptor KIR, is hybridized to a microarray or chip comprising panels of overlapping probes spanning a region of interest within one or more exons in the gene, such as an allele variation as in a single nucleotide polymorphism. The exon-specific primers may be labeled with a moiety or dye that produce a detectable signal. For example, with fluorophore-labeled primers, e.g., with a cyanine dye such as Cy3 or Cy5, which are exon specific. Hybridized amplicon-probe pairs can therefore be detected and hybridization patterns associated with an allelotype. A representative microarray design is disclosed in U.S. Pat. No. 7,354,710 and U.S. Publication Nos. 20070298425 and 20090011949 all to Hogan et al. and all hereby incorporated by reference. Also, for example, U.S. Publication No. 20070298425 discloses HLA primers to amplify HLA-A, HLA-B and HLA-DRB1 genes and HLA probe sequences accounting for allele variations in the HLA-A, HLA-B and HLA-DRB1 genes suitable for site-specific hybridization.

Alternatively, a nucleic acid sequence or length analysis may be performed on the second DNA or RNA amplicon using standard and known procedures, such as, but not limited to pyrosequencing. Such analysis is useful to obtain HLA types, or to obtain the identity and/or paternity of an individual. For example, length dependent analysis of nucleic acids is the basis for most current human identification via the short terminal repeat (STR)-based identifier reaction. Also, sequence or length analysis may provide useful forensic information from samples obtained at, for example, a crime scene. Furthermore, the tandem PCR reactions described herein may be performed on mitochondrial DNA for the purposes of human identification. Using mitochondrial DNA may be particularly useful when the sample is compromised, such as very small or degraded, because of its increased copy number. The tandem PCR methods provided herein are useful when the sample mitochondrial DNA comprises two hypervariable regions near the mitochondrial origin of replication and one or more additional mitochondrial genes. In addition, the tandem PCR reactions described herein may be performed on genes or gene sets other than HLA or KIR or mitochondrial DNA, particularly gene set analysis for the purposes of assessing disease risk or response to medication. Furthermore, the tandem PCR reactions may be performed on segments of microbe-specific microbial 16S DNA genes. Because microbial 16S DNA genes differ among microbes, the methods described herein are useful for detecting microbes present in the raw samples, for example, fecal matter.

Additionally, the instant methods are not limited to raw blood as the sample source. Most particularly, the methods can be used to process DNA- or RNA-containing specimens obtained by swabbing the inside of the mouth or the vaginal area, or a skin surface or other surfaces or objects. Furthermore, the swabbed surfaces or objects may be inanimate and the obtained sample may be processed via the instant methods to obtain evidence at a crime scene.

If the sample is fluid, as from a mouth or buccal swab, the resulting sample can be used directly, by squeezing the fluid from the swab, without DNA purification, to support tandem PCR or tandem RT-then-PCR as described herein. As with dried blood on paper cards, if the swab-containing sample is dry, or became dry after air-drying, it may be rehydrated and then, the resulting re-hydrated swab sample may be used, also without nucleic acid purification, to support the instant methods described herein.

The PCR amplification methods provided herein may be designed for performance on a system comprising a Laboratory on a Chip (LoC), for example, but not limited to, an HLA. The HLA-LoC replaces the entire workflow required for current, standard and well-known HLA-typing protocols with a single integrated workstation that requires only one technician for operation. A single technician needs only to load pre-fabricated chips and reagents into the workstation and to pipette the input blood specimens into the chip. Also, if necessary, one technician can tend to several stations in parallel. A hands-off duty cycle from sample loading to final HLA-type is less than 1 hour per specimen. The HLA-LoC is suitable for use in a doctor's office on an individual basis or field clinic among a population. In addition it is contemplated that with automation the HLA-Loc could become the standard for all HLA-typing labs.

Thus, an HLA-typing system comprises means for running tandem PCR, such as a PCR module, an HLA-LoC chip, a microarray platform for hybridization which includes a microarray reader and software for digitizing and analyzing hybridization data. The system also comprises the necessary processors and memory and storage components as required to operate the system and as are known and standard in the art. It is contemplated that all of the sample processing steps are automated in a simple cartridge format. Particularly, and without being limiting, the two analytical instruments comprising the system, i.e., the PCR module and microarray reader are integrated into one inexpensive device, using a modular architecture approach. With the modular approach this system can be optimized to meet various throughput requirements from those occurring at point-of-collection in a doctor's office or field clinic or, at the other extreme, those occurring in a centralized laboratory, such as in an ASHI-certified tissue typing laboratory.

The instant methods of HLA typing or analysis of other genes is not limited to Lab on a Chip applications. Via similar application of the instant tandem PCR methods, or the related application of tandem RT-then-PCR methods, the instant methods may also be used to enable HLA-typing without nucleic acid purification for batchwise processing (in a non Lab on a Chip format) as would be performed if the tandem reactions were performed in lots of 96 reactions in parallel, to be followed by analysis of the resulting secondary PCR amplicon by microarrays, or other methods of genetic analysis that could be performed in parallel.

It is contemplated that PCR #1+PCR #2 methods and systems may be used for other PCR-based genetic tests to replace the standard DNA purification+DNA quantitation+PCR steps. Also, it is contemplated that the method of HLA-typing provided herein is useful for other medical or health applications. For example, HLA-typing is required for solid organ transplantation and bone marrow and stem cell transplantation. In addition, the instant methods of HLA-typing may be useful for public health applications, such as, but not limited to, personalized vaccination responsiveness, HLA-based variation in infectious disease risk and HLA-based sensitivity to autoimmune diseases. Furthermore, it is contemplated that a purification free RNA analysis is useful as a diagnostic tool for early stage sepsis, or adverse drug reaction (ADR) using raw blood lymphocyte RNA expression as the analyte set of interest.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Tandem PCR Yields Constant 2° Product Over Wide 1° Input Amounts

2 µl of raw blood was used as the template for the primary, locus-specific HLA PCR reactions required for HLA-Chip analysis. Amplification was performed via the Finnzymes Phusion® Blood Direct kit. Different amounts of that primary, locus specific PCR product were then diluted in H2O and used as template for the secondary, self limiting, exon-specific PCR reactions. One microliter of each of the resulting 2° PCR reaction product was then loaded onto a standard acrylamide gel. HLA-A exons 2 and 3 and HLA-DRB1 exon 2 (FIG. 1A) and HLA-B exons 2 and 3 (FIG. 1B) were visualized by Amresco EZ-Vision DNA Dye. Positive controls on the gel refer to the product of the same tandem HLA PCR reactions, but instead using 10 ng of highly-purified Roche DNA as the original sample input. As seen, the amount of final 2° amplicon obtained from 2 µl of raw blood, is nearly independent of the amount of 1° amplicon used in the reaction, and similar in specificity & mass yield, to the amplified HLA product obtained from 10 ng of purified Roche DNA.

EXAMPLE 2

Generation of HLA Locus-Specific Amplicons

HLA locus-specific amplicons are generated from 2 µl whole fluid blood (FIG. 2A) via the PCR reaction using the Phusion Blood Direct® kit commercially available from Finnzymes (Woburn, Mass.). Reaction conditions are as follows: 1× Phusion® Blood PCR Buffer, 0.8 µl Phusion® Blood DNA Polymerase, 1.75 mM EDTA, 400 nM each primer in a 20 µl reaction volume. Reactions are cycled using the following protocol: initial denaturing at 98° C. for 5 minutes followed by 35 cycles of i) denature at 98° C. for 5 seconds, ii) anneal at 70° C. for 5 seconds, and iii) extend at 72° C. for 30 seconds, and one final extension at 72° C. for 1 minute.

When amplifying HLA loci from purified DNA (FIG. 2B), 10 ng of genomic DNA is used as template for PCR using Roche (Basel, Switzerland) FastStart Taq DNA Polymerase under the following conditions: 1×PCR Buffer (without Mg++), 1.5 mM MgCl2, 0.16 mg/ml BSA (fraction V), 0.05 µM each dNTP, 400 nM each primer, and 1 unit of Taq in a total reaction volume of 25 µl. These reactions are cycled using the following protocol: initial denaturing at 98° C. for 5 minutes followed by 35 cycles of i) denature at 98° C. for 5 sec, ii) anneal at 70° C. for 1 minute, and iii) extend at 72° C. for 30 sec, then a final 72° C. extension for 7 minutes.

HLA Locus Specific Primary PCR Primer Sequences

```
HLA-A locus primary primer pair:
Forward primer 1:
                                  (SEQ ID NO: 1)
5'-GCC TCT GYG GGG AGA AGC AA-3'

Reverse primer 1:
                                  (SEQ ID NO: 2)
5'-GTC CCA ATT GTC TCC CCT CCT T-3'

HLA-B locus primary primer pair set:
Forward primer 2a:
                                  (SEQ ID NO: 3)
5'-GGG AGG AGC GAG GGG ACC GCA G-3'

Forward primer 2b:
                                  (SEQ ID NO: 4)
5'-GGG AGG AGA GAG GGG ACC GCA G-3'

Forward primer 2c:
                                  (SEQ ID NO: 5)
5'-GGG AGG AGC AAG GGG ACC GCA G-3'

Reverse primer 1:
                                  (SEQ ID NO: 6)
5'-GGA GGC CAT CCC GGG CGA TCT AT-3'

Reverse primer 3:
                                  (SEQ ID NO: 7)
5'-GGA GGC CAT CCC CGG CGA CCT AT-3'

Reverse primer 3a:
                                  (SEQ ID NO: 8)
5'-TTC TCC ATT CAA CGG AGG GCG ACA-3'

Reverse primer 3b:
                                  (SEQ ID NO: 9)
5'-TTC TCC ATT CAA GGG AGG GCG ACA-3'

HLA-DRB1 locus primary primer pair set:
Forward primer 1a:
                                  (SEQ ID NO: 10)
5'-CTT GGA GGT CTC CAG AAC AGG-3'

Forward primer 1b:
                                  (SEQ ID NO: 11)
5'-CTT AGA GGT CTC CAG AAC CGG-3'

Reverse primer 4-xx:
                                  (SEQ ID NO: 12)
5'-CAC ACA CAC ACA CAC ACT CAG ATT C-3'

Reverse primer 4-07:
                                  (SEQ ID NO: 13)
5'-CAC ACA CAC AAC CAC ACT CAG ATT C-3'

Reverse primer 4-10:
                                  (SEQ ID NO: 14)
5'-CAC ACA CAC ACA CAG AGT CAG ATT C-3'
```

Figure 4B:
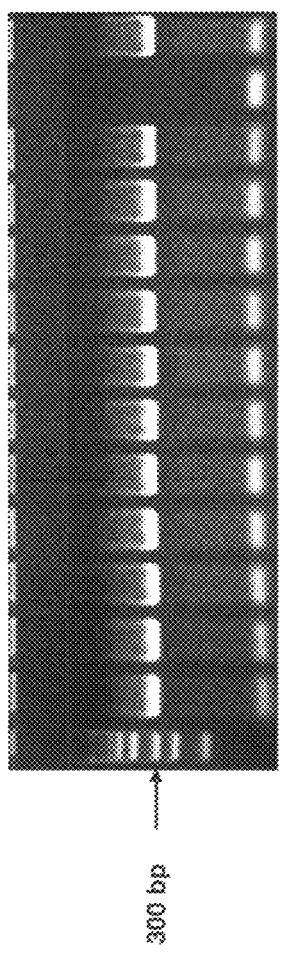
Figure 4C:
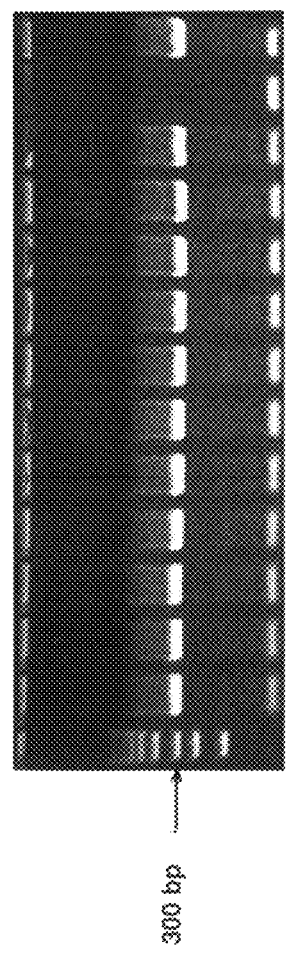

The product from the locus-specific reactions (FIGS. 3A-3C), diluted 1:100 in molecular biology grade water, are used as a template for subsequent exon-specific "nested" PCR reactions (FIGS. 4A-4C). PCR reactions are performed using Applied Biosystems' (Foster City, Calif.) Amplitaq Gold® DNA Polymerase in a 100 µl reaction volume with the following components: 5 µl of 1:100 diluted locus specific PCR product, 1×PCR Buffer 11, 1.5 mM MgCL2, 0.16 mg/ml BSA (fraction V), 0.2 mM each dNTP, 400 nM each primer, and 4 units of Amplitaq Gold® DNA Polymerase. Cycling conditions are: initial denaturation at 94° C. for 2 minutes followed by 40 cycles of (i) denaturing at 98° C. for 30 seconds, (ii) annealing at 68° C. for 30 seconds, and (iii) extension at 72° C. for 30 seconds, then a final extension step of 72° C. for 7 minutes. Exon-specific PCR primers are labeled with Cyannine 3 dye to facilitate detection of positive hybridization events by laser excitation/emission in a microarray scanner such as a ProScan Array HT (Perkin-Elmer, Waltham, Mass.).

Exon Specific Secondary PCR Primer Sequences

HLA-A Exon 2 Secondary Primer Pair:

```
Forward primer 2b-24:
                                  (SEQ ID NO: 15)
5'-(cy3) AGC CTG GTT CAC TSC TCG YCC CCA GGC
TC-3'

Reverse primer 2a-28:
                                  (SEQ ID NO: 16)
5'-(cy3) TAC TAC AAC CTT GCC TCG CTC TGG TTG
TAG TAG C-3'
```

HLA-A Exon 3 Secondary Primer Pair:

```
Forward primer 2b-24:
                                    (SEQ ID NO: 17)
5'-(cy3) GTG AGA ACT AGT CSG GGC CAG GTT CTC
ACA-3'

Reverse primer 2b-26:
                                    (SEQ ID NO: 18)
5'-(cy3) GTA CCA GGT TCC CGT GGC CCC YGG TAC
C-3'
```

HLA-B Exon 2 Secondary Primer Pair:

```
Forward primer 2c-20:
                                    (SEQ ID NO: 19)
5'-(cy3) ACC CTC TTG AGC CGC GCC GGK AGG AGG
GTC-3'

Reverse primer 2a-28:
                                    (SEQ ID NO: 20)
5'-(cy3) TAC TAC AAC CTT GCC TCG CTC TGG TTG TAG
TAG C-3'
```

HLA-B Exon 3 Secondary Primer Pair:

```
Forward primer 2a-22:
                                    (SEQ ID NO: 21)
5'-(cy3) GTG AGA CTT ACC GGG GCC AGG GTC TCA
CA-3'

Reverse primer 2a-26:
                                    (SEQ ID NO: 22)
5'-(cy3) GTA CCA GGT TCC CAC TGC CCC TGG TAC
C-3'
```

DRB1 Exon 2 Secondary Primer Pair Set:

```
Forward primer 3-xx-24:
                                    (SEQ ID NO: 23)
5'-(cy3) AAC GTG CTT TTT CGT GTC CCC ACA GCA CGT
TTC-3'

Forward primer 3-04-24:
                                    (SEQ ID NO: 24)
5'-(cy3) AAC GTG CTT TTT CTT GTC CCC CCA GCA CGT
TTC-3'

Forward primer 3-07-24:
                                    (SEQ ID NO: 25)
5'-(cy3) AAC GTG CTT TTT TGT GCC CCC ACA GCA CGT
TTC-3'

Reverse primer 3-xx-20:
                                    (SEQ ID NO: 26)
5'-(cy3) TGC AGC TTT GCT CAC CTC GCC GCT GCA C-3'

Reverse primer 3-09-22:
                                    (SEQ ID NO: 27)
5'-(cy3) TGC AGA GTT GCT TAC CTC GCC TCT GCA C-3'
```

Exon-specific PCR's, amplified in a single PCR reaction as a set, are used as target in self assembling single base discriminatory microarray hybridizations using the following procedure: Microarray slides are pre-rinsed with ddiH2O at 40° C. for 15 minutes before assembling into Grace Bio-Labs (Bend, Oreg.) ProPlate Multi-Array Slide System. Each of the 16 wells on a microarray slide/Poroplate superstructure is equilibrated with 75 µl pre-hybridization buffer consisting of 3×SSC (Sigma-Aldrich, St. Louis, Mo.) and 5×Denhardt's Solution (Amresco, Inc. Solon, Ohio). Target PCR product is combined with other reagents to make a hybridization cocktail consisting of 3×SSC, 5×Denhardt's Solution, and 50% exon-specific PCR product. This cocktail is then denatured for 5 minutes at 99° C. followed by snap-cooling to −20° C. for 3 minutes immediately prior to hybridization to a genotyping microarray. Denatured PCR product is applied to previously equilibrated microarrays and are allowed to hybridize at 25° C. for 16 hours. After hybridization arrays are washed twice with 100 µl per well of 0.2×SSC for 15 minutes each wash. Array cassettes are disassembled and slides are washed in bulk format briefly with 0.2×SSC then dried by centrifugation at 60×g in an Eppendorf 5810 centrifuge. Fluorescence data is acquired by scanning slides in a Perkin-Elmer Scan-Array Lite laser scanner using Cyannine3 and Cyannine5 channels set for 60% and 40% PMT gain, respectively. Resulting data files, consisting of a quantitative fluorescence measurement for each probe feature on a microarray slide, are analyzed by software developed by Genomics USA in order to generate HLA genotype calls.

EXAMPLE 3

Lab-on-a-Chip Microarray Platform

The LoC microarray platform (In-Check™) system integrates PCR amplification and microarray detection processes for genetic testing in a single lab-on-a-chip. The system is designed for identification of complex nucleic-acid analytes, such as in HLA-typing, by integrating PCR amplification and hybridization on a single low-density microarray. The system is based on a technology that monolithically integrates a PCR micro-reactor fluidically connected with a hybridization reactor composed of a low-density microarray on a miniaturized silicon lab-on-chip (LoC).

PCR Module

The PCR module (In-Check™) has integrated silicon heaters, temperature sensor and miniaturized 25 µl volume which allow the PCR module to perform the rapid heating and cooling cycles required for highly reliable, end-point PCR. The PCR module is thermally driven by the temperature control system (TCS; In-Check™). The TCS allows fast and programmable temperature cycling in a way that allows 5 different LoC tests to be performed in parallel.

Lab-on-Chip

The LoC is a disposable device that is manufactured using silicon-semiconductor MEMS technology and is mounted on a 1"×3" plastic slide that provides the necessary mechanical, thermal & electric connections. The silicon chip is an electrically active system that monolithically integrates a 25 µl PCR reactor with a hybridization area of 30 µl that hosts a low density microarray of up to 500 spots in 1 cm2. Accurate temp control is maintained through 3 resistive heaters and temp sensors located above the PCR reactor.

Microarray Hybridization and Detection

Up to 500 probe spots can be positioned within the 1 cm×1 cm microarray module of the LoC chip. The microarray module is fluidically connected to the PCR chambers on the LOC (In-Check™) and is coupled to an on-chip temperature control system, thus allowing full temperature control during hybridization and washing. After hybridization, the microarray module is read by inserting the entire 1"×3" LoC into the microarray optical reader (OR; In-Check™). Depending on the resolution required, scanning by the OR typically takes less than 60 seconds, followed by direct data transfer to additional software, such as Ricimer (GenUSA, www.GenomicsUSA.com), for genotyping. Samples are applied directly to the LoC with ordinary lab tools via the loading station. All processing can be performed by staff with only routine biochemical training. It is expected with raw blood as the sample input, as many as 50 HLA-Loc tests could be done per day, per workstation (5 at a time on the PCR module) with essentially only a manual pipetting as the requisite lab equipment.

EXAMPLE 4

Microarray Image Processing

For clinical and epidemiological applications of the HLA-Chip, it is necessary to automatically digitize raw microarray image data, and then to convert those image data into allele-specific probe calls, in accord with the relationship between probe hybridization and (local) allele structure that we have described already.

Automated Array Digitization

Numerical analysis of a microarray image is based on "spot finding" and the integration of hybridization signal intensity, within a spot, once circumscribed. Such spot finding and integration is now a routine functionality in imager software. Automated image analysis by employing the use of a Cy5 labeled 25mer Oligo-dT oligonucleotide, which has been doped at 5% density within each probe element printed onto the array. By introducing such a marker and using both standard optical channels of the imager (Cy5 for the marker and Cy3 for the hybridization signal) it is possible to localize each probe spot, independently of others: in a sense, the number of fiducial markers equals that of the hybridization signals, to create redundancy.

Automated Assembly of Allele-Specific Probe Hybridization Data into an HLA-Allelotype After reading in the raw data, the probe map, and all known allele sequences for the relevant gene, the Ricimer software determines allele calls based on the presence or absence of hybridization signal from the printed probes. This is accomplished by what is in essence a two-stage process of elimination. The first stage involves examining each probe that is reported to be "off" and comparing the sequence of that probe with the known allele sequences. If an allele's sequence matches the sequence of one or more of the "off" probes then that allele is eliminated as a candidate, as it cannot be one of the pair of alleles present in the sample.

Once this first stage is complete, the set of candidate alleles has been dramatically reduced. At this point every possible pairing of the remaining alleles is evaluated separately. Each allele pair is compared to the entire set of "on" probes as reported by the array. If there is any discrepancy between the experimentally measured "on" probe set and the expected "on" probe set predicted by the allele sequences, that allele pair is no longer considered a candidate for the solution set. After these two culling steps have been performed, all possible pairings of alleles that can account for the data have been determined and are reported to the user. Typically a calculated probability value based on the worldwide population frequency of the alleles present in the pairings is also reported to assist the user in making a decision. This very powerful allele calling statistical functionality became the basis for the graphical interphase that presents to the user, the certainty of the experimental HLA-type and all possible alternative allele calls.

EXAMPLE 5

PCR Reactions for HLA-Typing from Raw Blood in the Fluid State and from Raw Blood that was Allow to Dry on Guthrie cards Raw anonymized raw blood was obtained from Memorial Blood Labs, Minneapolis Minn. and was stored frozen at −20 C until needed. Thawed raw blood was used directly as the template for the primary, locus-specific HLA PCR reactions required for HLA-Chip analysis. The corresponding dried blood samples were prepared by pipetting fresh, never frozen, blood onto standard Whatman-GE Guthrie cards, followed by 72 hrs of drying at 25 YC in a laminar flow hood, then storage in a sealed pouch, at 25 YC, thereafter. For dried blood on Guthrie cards, a 2 mm circular punch was excised from the blood card, to which was added 100 µl of 100 mM Boric acid and 1 mM EDTA at pH 7.5. The punch was then heated for 2 hrs 70 C to rehydrate the blood spot, and to elute the contents of blood spot into solution. The resulting fluid phase was then mixed by pipetting. The rehydrated punches were then stored at −20 YC until analysis.

For both raw and rehydrated dried blood, 1 µl of sample was used without subsequent purification as the template for PCR. A first PCR amplification was performed via the Finnzymes Phusion® Blood Direct kit. 1 µl of that primary, locus specific PCR product was then applied directly as template for the secondary, self limiting, exon-specific PCR reactions. One microliter of each of the resulting 2° PCR reaction product was then loaded onto a standard acrylamide gel. HLA-A exons 2 and 3 and HLA-DRB1 exon 2 (FIG. 5A) and HLA-B exons 2 and 3 (FIG. 5B-5C) were visualized by Amresco EZ-Vision DNA Dye. Positive controls on the gel refer to the product of the same tandem HLA PCR reactions, but instead using 10 ng of highly-purified Roche DNA as the original sample input. As seen, the amount of final 2° amplicon obtained from 1 µl of raw blood, is nearly independent of the sample used in the reaction, and similar in specificity & mass yield, to the amplified HLA product obtained from 10 ng of purified Roche DNA.

EXAMPLE 6

PCR Reactions for HLA-Typing from Rehydrated Buccal Swabs

De-identified buccal swabs were procured from local donors. Four swabs were collected from each participant by vigorously swabbing up and down twenty times per each quadrant of the mouth and placed into 15 mL conical tubes. Whole mouth swabs were taken from 12 individuals: A1-A12. Samples were dried for 72 hours under laminar flow hood. Dried swabs were then rehydrated in 150 µl of rehydration buffer (100 mM Borate+1 mM EDTA) and solubilized at 70 YC for 2× hours. The resulting fluid phase was then mixed by pipetting. The rehydrated swabs were then stored at −20 YC until analysis. A nested (tandem) PCR reaction was then performed for each of the HLA loci of interest. 1 µl of raw swab eluate was used for a primary 25 µL PCR reaction employing Roche Taq polymerase'. The subsequent (secondary) PCR was then performed upon 2.5 µL of the primary amplicon product in a total PCR reaction volume of 25 µL, also employing Roche Taq polymerase. Upon completion, the residual sample (up to half the recovered volume) was extracted via QIAamp DNA Blood Mini Kit (Qiagen catalog #51104). The resulting purified DNA was run on the same microarray HLA-typing platform. Unpurified and purified buccal DNA were analyzed via microarray technology for HLA typing. The matched, de-identified DNA from buccal swabs was compared to HLA types obtained on the raw, unpurified samples via gel electrophoresis. One microliter of each of the resulting 2° PCR reaction product was then loaded onto a standard acrylamide gel.

Figure 6A:
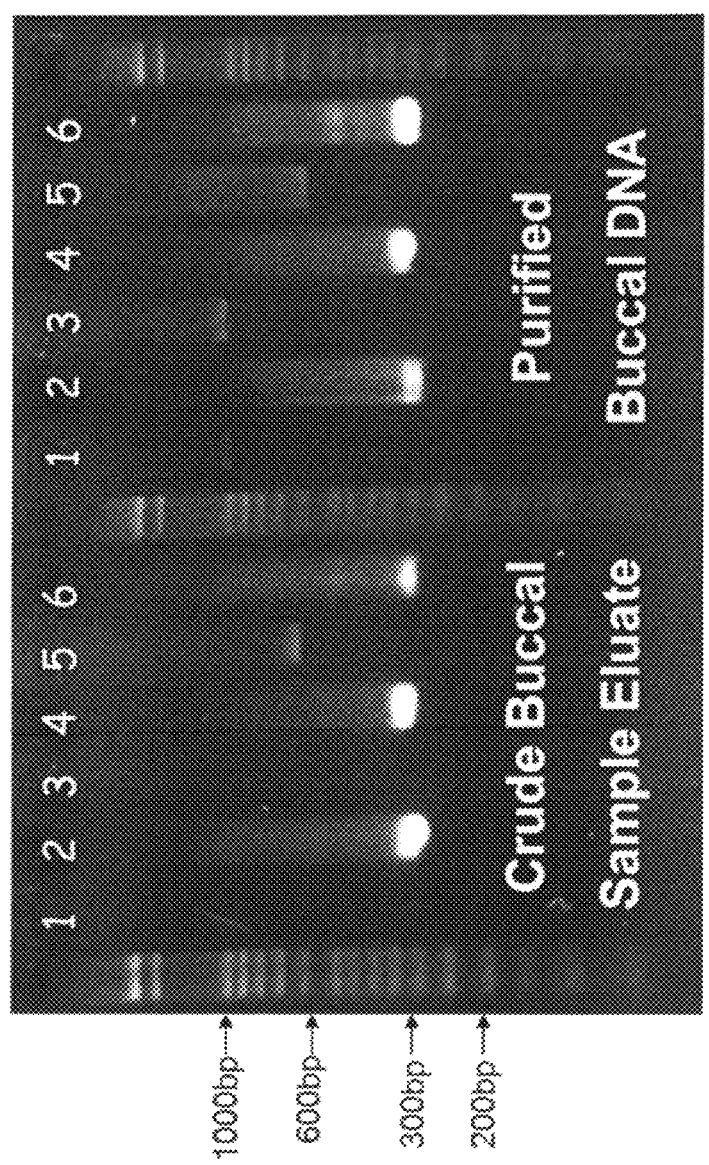
FIGS. 6A-6G show PCR reactions for HLA-typing from rehydrated buccal swabs. De-identified buccal swabs were procured from local donors. Four swabs were collected from each participant by vigorously swabbing up and down twenty times per each quadrant of the mouth and placed into 15 mL conical tubes. Whole mouth swabs were taken from 12 individuals: A1-A12. Samples were dried for 72 hours under laminar flow hood. Dried swabs were then rehydrated in 150 μl of rehydration buffer (100 mM Borate+1 mM EDTA) and solubilized at 70 YC for 2× hours. The resulting fluid phase was then mixed by pipetting. The rehydrated swabs were then stored at −20 YC until analysis. A nested (tandem) PCR reaction was then performed for each of the HLA loci of interest. 1 μl of raw swab eluate was used for a primary µLPCR reaction employing Roche Taq polymerase'. The subsequent (secondary) PCR was then performed upon 2.5 µL of the primary amplicon product in a total PCR reaction volume of 50 µL, also employing Roche Taq polymerase. Upon completion, the residual sample (up to half the recovered volume) was extracted via QIAamp DNA Blood Mini Kit (Qiagen catalog #51104). The resulting purified DNA was run on the same microarray HLA-typing platform. Unpurified and purified buccal DNA were analyzed via microarray technology for HLA typing. The matched, de-identified DNA from buccal swabs was compared to HLA types obtained on the raw, unpurified samples via gel electrophoresis. 2.5 microliters of each of the resulting 2° PCR reaction product was then loaded onto a standard agarose gel. Primary locus specific PCR products as well as the products of the secondary exon specific reaction set (performed as a single multiplex reaction) were displayed in FIG. 6A (left) along with identical reaction products obtained from 10 ng of purified DNA obtained from the sample (right). Bands were visualized by Amresco EZ-Vision DNA Dye. As seen, the amount of final 2° amplicon obtained from 1 µL of raw swab eluate, is similar in specificity & mass yield, to the amplified HLA product obtained from 10 ng of purified DNA from the same sample.
Figure 6B:
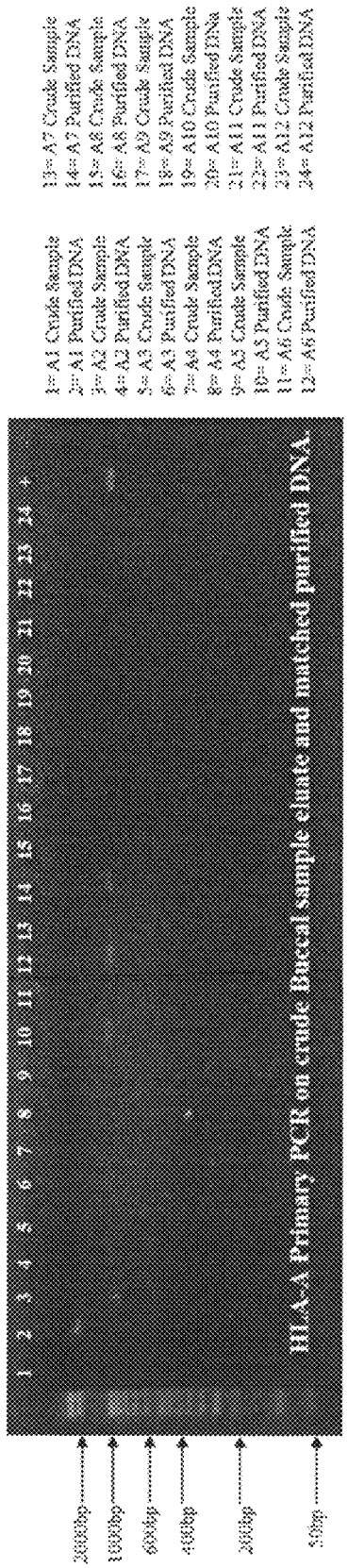
Figure 6C:
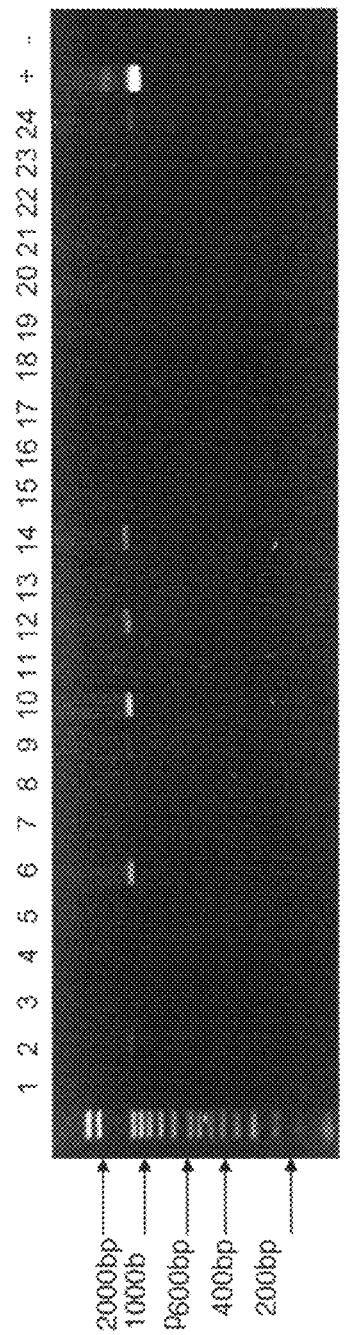
Figure 6D:
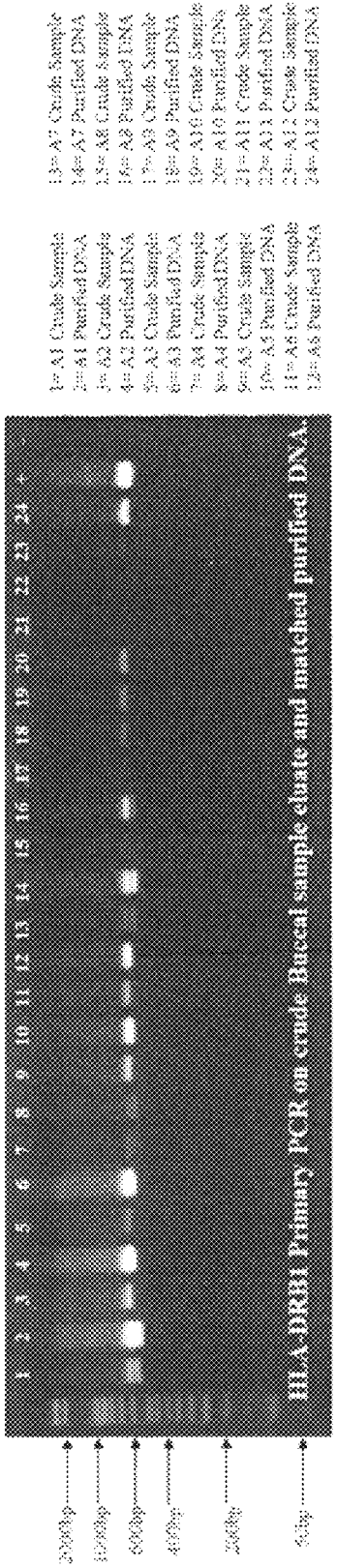
Figure 6E:
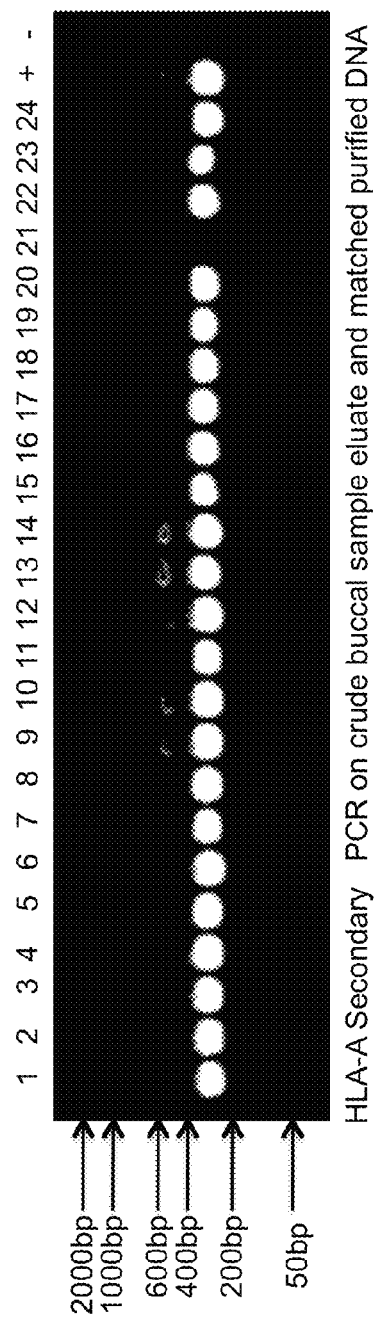
Figure 6F:
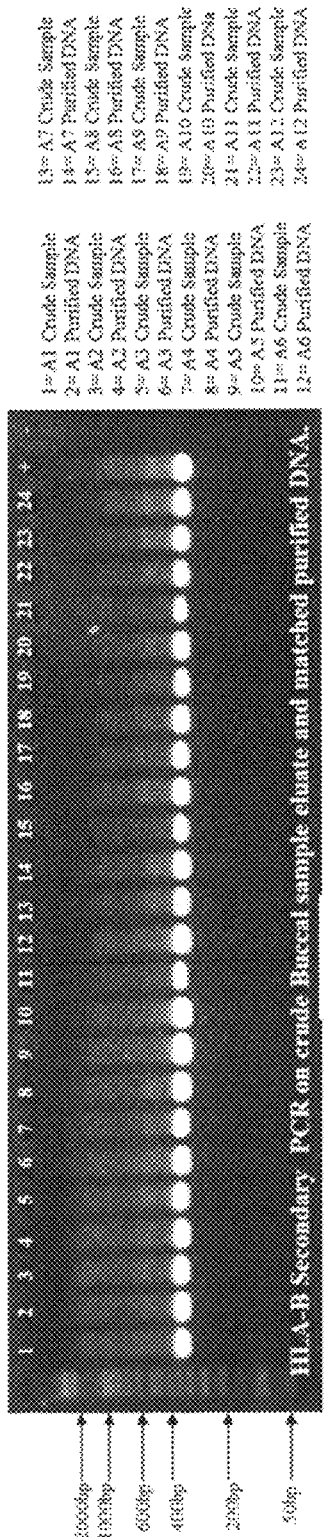
Figure 6G:
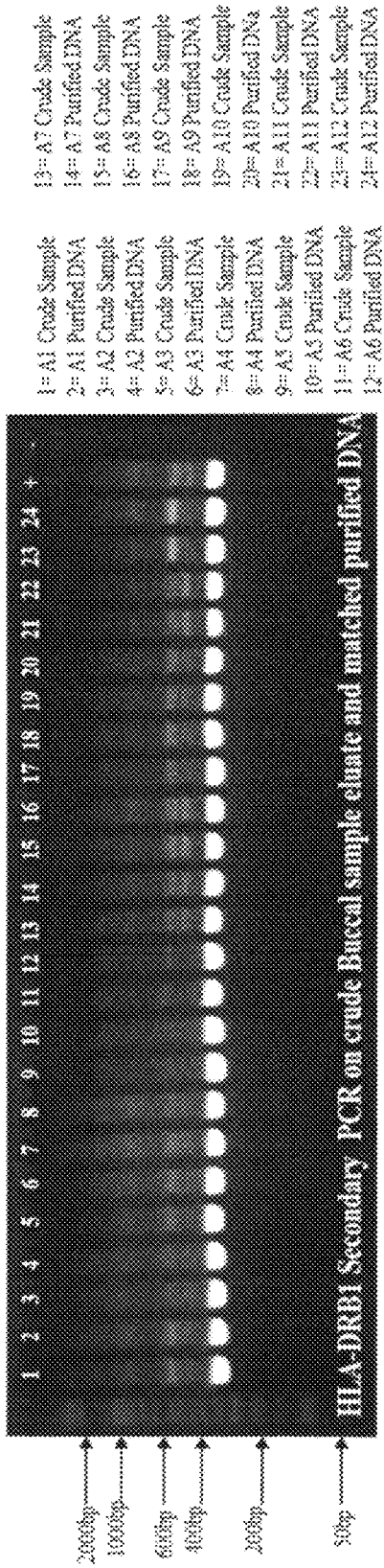

Primary locus specific PCR products as well as the products of the secondary exon specific reaction set (performed as a single multiplex reaction) were displayed in FIG. 6A (left) along with identical reaction products obtained from 10 ng of purified DNA obtained from the sample (right). Bands were visualized by Amresco EZ-Vision DNA Dye. As seen, the amount of final 2° amplicon obtained from 1 µL of raw swab eluate, is similar in specificity & mass yield, to the amplified HLA product obtained from 10 ng of purified DNA from the same sample. FIGS. 6B-6G display the product of the tandem PCR reactions performed on raw cheek swabs from a total of 12 donors. FIGS. 6B-6D display the primary PCR reactions specific for HLA-A, HLA-B & HLA-DRB1 for these 12 raw buccal swab samples, while FIGS. 6E-6G display the secondary PCR reactions specific for HLA-A, HLA-B & HLA-DRB1 for the sample 12 raw buccal swab samples. As can be seen, although the yield of primary PCR product is highly variable among the set of 12 raw, re-hydrated buccal swabs samples (FIGS. 6B-6D) the subsequent secondary PCR reaction has generated a series of amplified exons which are nearly identical in yield and specificity, among the set of 12 raw buccal swab specimens (FIGS. 6E-6G).

EXAMPLE 7

Multiplex PCR from Purified DNA, for Several Genes in Parallel

HLA locus-specific amplicons for HLA-A plus HLA-DRB1, and HLA-B and HLA-DRB1 are generated from 1 µl whole fluid blood (FIG. 7A-7B, 7G-7H) via the PCR reaction using FastStart Taq DNA Polymerase under the following conditions: 1×PCR Buffer (without $Mg^{++}$), 1.5 mM $MgCl_2$, 0.16 mg/ml BSA (fraction V), 0.05 µM each dNTP, 400 nM of each locus-specific primer for each of the genes being amplified in parallel, and 1 unit of Taq in a total reaction volume of 25 µl. These reactions are cycled using the following protocol: initial denaturing at 98° C. for 5 minutes followed by 35 cycles of i) denature at 98° C. for 5 sec, ii) anneal at 70° C. for 1 minute, and iii) extend at 72° C. for 30 sec, then a final 72° C. extension for 7 minutes.

Figure 7A:
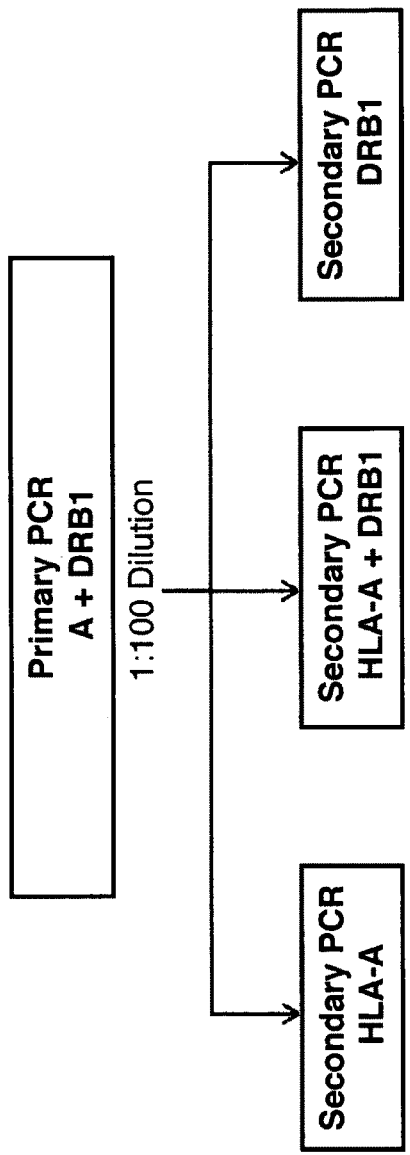
Figure 7B:
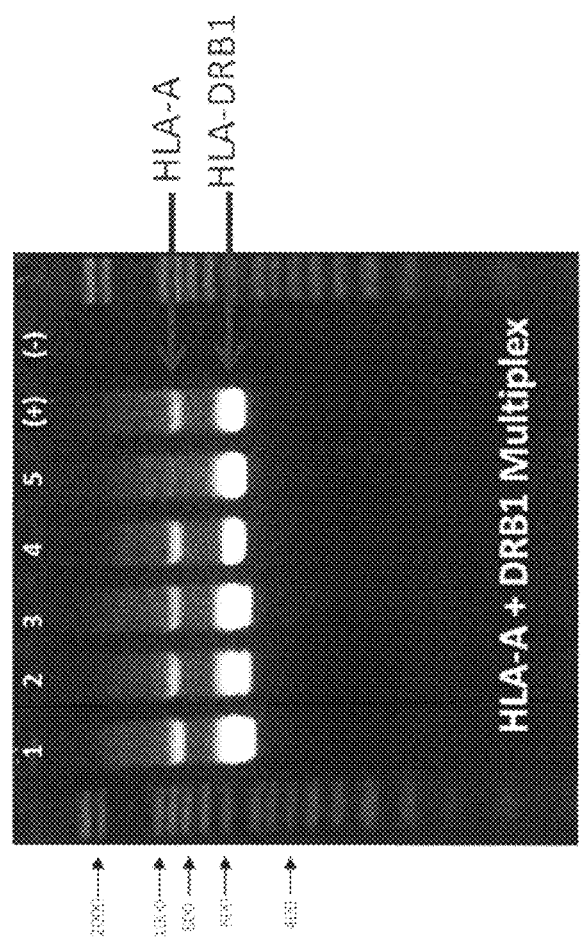
Figure 7F:
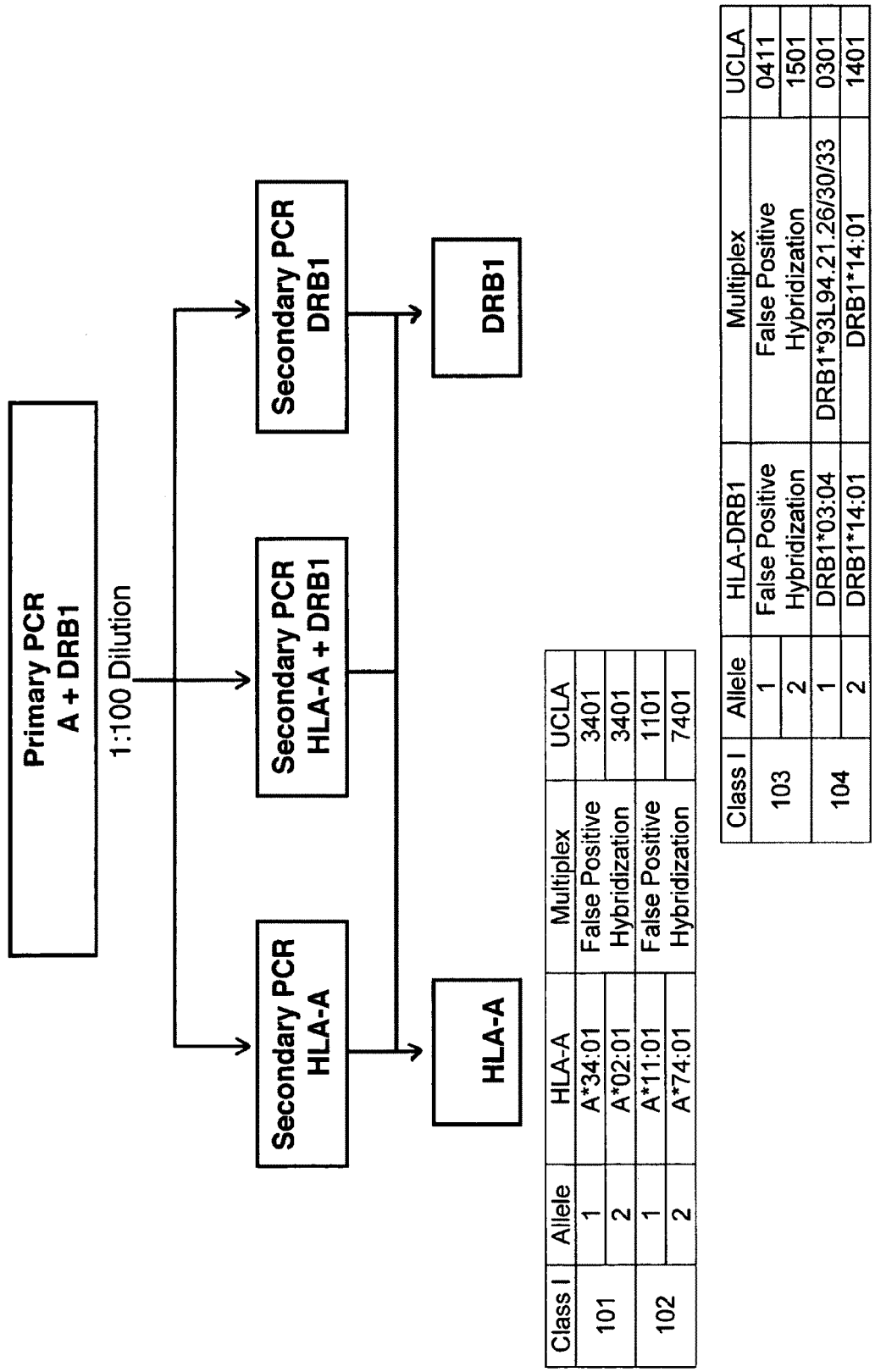
Figure 7G:
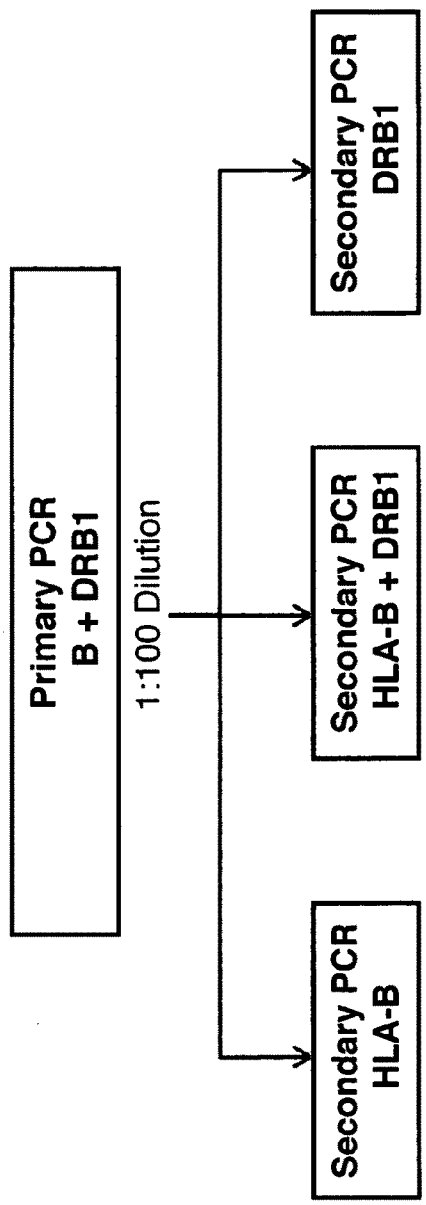
Figure 7L:
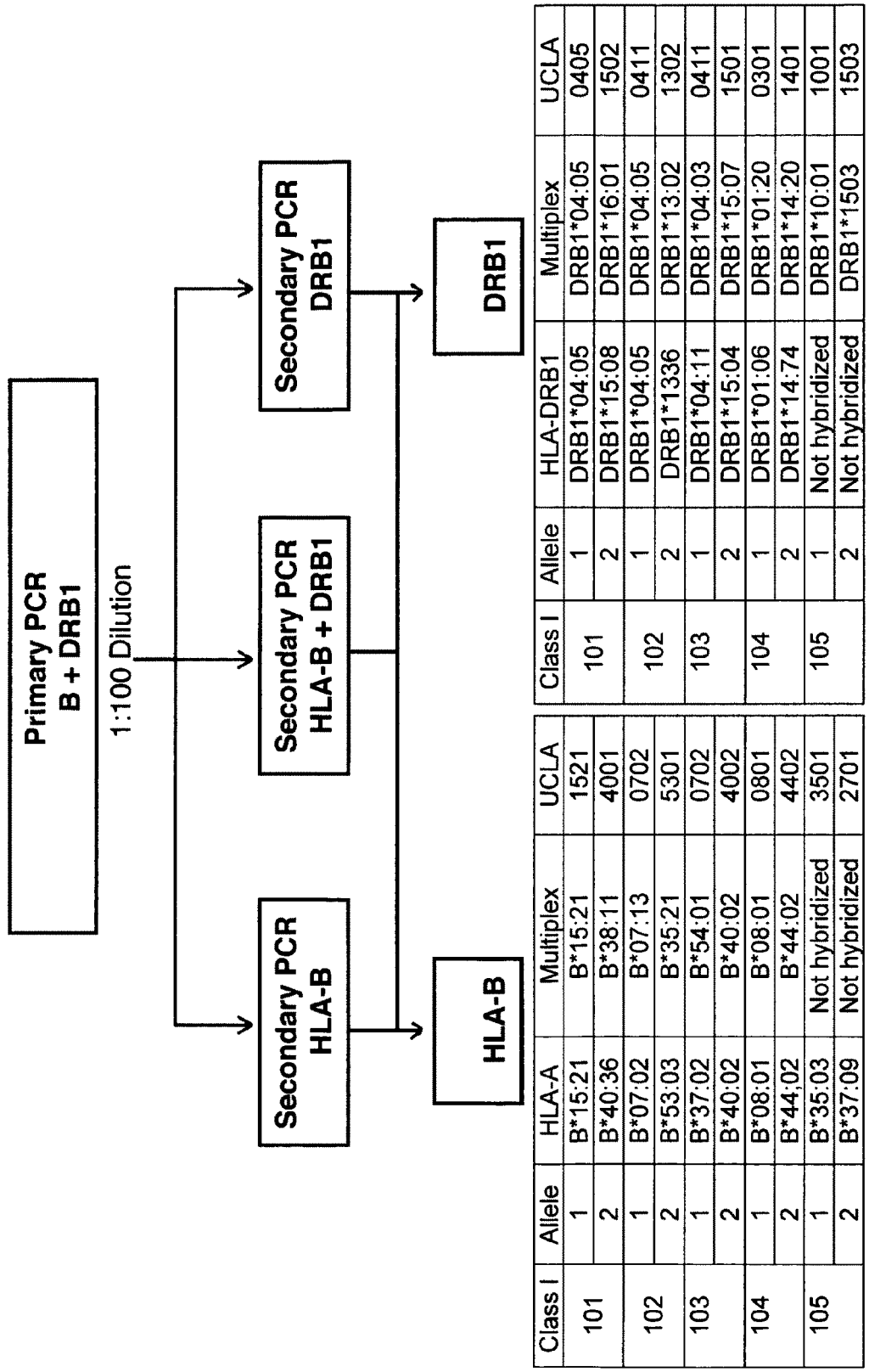

The product from the locus-specific reactions of HLA-A and DRB1 performed in parallel and HLA-B and HLA-DRB1 also performed in parallel (FIGS. 7B,7H), diluted 1:100 in molecular biology grade water, are used as a template for subsequent exon-specific "nested" PCR reactions (FIGS. 7C-7E, 7I-7K). As shown on the diagrams of FIGS. 7A and 7G the dilution of the locus-specific PCR were used as template for an exon-specific PCR reaction where either only HLA-A, HLA-DRB1 or HLA-B exons were amplified. A second reaction can be performed were the exons 2 and 3 for HLA-A or HLA-B can be simultaneously amplified with exon 2 from HLA-DRB1. The above mentioned PCR reactions are performed using Applied Biosystems' (Foster City, Calif.) Amplitaq Gold® DNA Polymerase in a 100 µl reaction volume with the following components: 5 µl of 1:100 diluted locus specific PCR product, 1×PCR Buffer II, 1.5 mM $MgCL_2$, 0.16 mg/ml BSA (fraction V), 0.2 mM each dNTP, 400 nM each primer of interest, and 4 units of Amplitaq Gold® DNA Polymerase. Cycling conditions are: initial denaturation at 94° C. for 2 minutes followed by 40 cycles of (i) denaturing at 98° C. for 30 seconds, (ii) annealing at 68° C. for 30 seconds, and (iii) extension at 72° C. for 30 seconds, then a final extension step of 72° C. for 7 minutes. Exon-specific PCR primers are labeled with Cyannine 3 dye to facilitate detection of positive hybridization events by laser excitation/emission in a microarray scanner such as a ProScan Array HT (Perkin-Elmer, Waltham, Mass.). Hybridization of the genes amplified in parallel are performed where the products of the secondary amplification of exons 2 and 3 of HLA-A and HLA-B, and exon 2 of HLA-DRB1 can be hybridized to the corresponding HLA-Chips obtaining successful matching genotypes in preliminary data collection (FIG. 7F) In addition, the product of the secondary PCR of genes amplified in parallel such as HLA-A and HLA-DRB1 can be hybridized to either an HLA-A chip or an HLA-DRB1 chip, the same applies for the secondary PCR product of HLA-B and HLA-DRB1 multiplex (FIG. 7L).

EXAMPLE 8

Multiplex PCR of DNA from Raw Unpurified Fecal Matter for Several Genes in Parallel Analysis of the DNA complement of feces has become very important for the clinical and research analysis of microbial diversity in feces, and the relationship between that diversity and human or animal diseases. It is well known that, among prokaryotic microbes, individual microbes can be identified based on variation in the sequence of their 16S gene and the 16S rRNA expressed from it. It is also well known that 16S DNA can be amplified using "universal" PCR primer sets which, when used as a set, will amplify all members of the prokaryotic 16S RNA gene family, so that the amplified DNA can be analyzed by sequence analysis on microarrays or by chemical or biochemical sequencing methods. Although such 16S DNA sequence analysis can be performed by all such methods to yield an estimate of the type of prokaryotic microbe in a specimen, that kind of analysis in feces has proven difficult to implement in large clinical or field studies, due to the cost and health risks associated with DNA purification from fecal matter.

It is well known that the microbial content of ordinary human stool comprises $10^{+10}$ up to $10^{+11}$ microbes per CC, which is nearly 1% by mass. Based on that very high cell density, the density of 16S gene DNA in those same samples will therefore also exceed $10^{+10}$ up to $10^{+11}$ 16S gene segments per CC, or about $10^{+7}$ copies per µl. The tandem PCR reactions of the kind described in Examples 1-9 function well on about 10 ng human DNA (about 2,000 copies) per µl. Thus, at ordinary microbial density in feces, 16S DNA is presented at a copy number density that is at least 1,000 times greater than displayed in Examples 1-9 for raw blood or buccal swabs. Based on that very high copy number, it is therefore possible to use the technology described herein to perform 16S DNA based microbial diversity analysis upon unpurified fecal matter:

Step 1. Obtain about 10 µl (about 10 $mm^3$) of feces by contact transfer with a stick or tip.

Step 2. Dissolve the feces in about 100 µl of water.

Step 3. Take about 1 µl of diluted feces suspension and perform a primary 16S PCR reaction with a universal 16s PCR primer set.

Step 4. Take 1 µl of the primary PCR amplicon product set from PCR reaction #1, dilute it ten fold, then apply 1-2 µl of that diluted primary amplicon mix as template for a second PCR reaction which can be initiated with the same universal 16S DNA primer set used in the first PCR reaction, or a primer set which targets a subset of the 16S PCR gene amplified in the primary reaction.

Step 5. The secondary PCR reaction is diluted in hybridization buffer and analysed via hybridization to a microarray which contains probes which are specific to variations of the 16S gene sequence that are know to distinguish one prokaryotes in a mixture of prokaryotes: the result being 16S DNA based analysis of a set of prokaryotic organisms in a way that bypasses DNA purification prior to analysis.

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will appreciate readily that the present invention is well adapted to carry out the objects and obtain the ends and advantages mentioned, as well as those objects, ends and advantages inherent herein. The present examples, along with the methods, procedures and systems described herein are presently representative of preferred embodiments, are exemplary, and are not intended as limitations on the scope of the invention. Changes therein and other uses will occur to those skilled in the art which are encompassed within the spirit of the invention as defined by the scope of the claims.

---

What is claimed is:

1. A method for amplifying a DNA of interest, comprising:
obtaining a raw sample comprising DNA;
performing a first PCR on the raw sample to produce a first amplicon;
diluting the first amplicon; and
performing a second PCR thereon until all primers used in the second PCR reaction are consumed to produce a second amplicon, thereby amplifying the input sample DNA to a final amplified DNA product concentration that is limited by the primer concentration in the second PCR reaction, said second PCR reaction independent of the amount or purity of the DNA comprising the original sample, wherein primers for the second PCR reaction target DNA sequences that are contained within the amplified product of the first PCR reaction and wherein primers for the second PCR reaction are a set of multiple exon-specific primers having sequences shown in at least SEQ ID NO:15 and 16 and additional primer pairs selected from the group consisting of SEQ ID NOs:17-27.

2. The method of claim 1, comprising:
performing the first PCR on a set of gene targets in parallel on the raw sample to produce a first set of amplicons;
diluting the first set of amplicons; and
performing a second PCR thereon, using the entire set of primary amplicon products as a set of templates for the second PCR reaction until all secondary PCR primers are consumed to produce a second amplicon set, thereby amplifying the DNA.

3. The method of claim 2, wherein less than 5 gene targets, less than 10 gene targets or less than 20 gene targets are amplified in parallel.

4. The method of claim 2, wherein the gene targets are HLA-DRB1, DQ-A1 and DQB1; are DQ-A1 and DQ-B1 or are HLA-B and KIR.

5. The method of claim 2, wherein the gene targets are two hypervariable regions near the mitochondrial origin of replication and one or more additional mitochondrial genes.

6. The method of claim 2, wherein the gene targets are segments of microbe-specific microbial 16S DNA genes, said method detecting microbes in the raw samples.

7. The method of claim 1, further comprising labeling the second PCR primers with one or more fluorophores.

8. The method of claim 7, wherein the fluorophor is a cyanine dye.

9. The method of claim 8, wherein the DNA comprises one or more genes of interest, further comprising:
hybridizing the second amplicon to probes having sequences of allele variations associated with the gene of interest;
detecting a fluorescence pattern from the hybridized amplicon; and
assigning an allelotype based on the fluorescence pattern.

10. The method of claim 9, wherein the gene(s) of interest are an HLA-A gene, an HLA-B gene, an HLA-DRB1 gene, an HLA-DQA1 gene, or an HLA-DQB1 gene.

11. The method of claim 1, wherein primers for the first PCR are locus-specific primers.

12. The method of claim 11, wherein the primers have sequences shown in SEQ ID NOS: 1-14.

13. The method of claim 1, further comprising:
sequencing the second amplicon for an analysis thereof.

14. The method of claim 13, wherein analysis determines one or more of identity, paternity of an individual, forensic information, tissue matching, risk factors for the development of disease, or response to medication.

15. The method of claim 1, wherein the raw sample is fresh or rehydrated and comprises unprocessed fluid blood, dried unprocessed blood, a fresh buccal swab sample, a dried buccal swab sample, fecal material, a vaginal sample or a sample obtained by swabbing an animate or inanimate surface or object.

16. The method of claim 1, wherein the DNA is mitochondrial DNA.

17. A method for amplifying one or more RNAs of interest, comprising:
obtaining a raw biological sample from an individual;
performing a first reverse transcription PCR on the raw biological sample to produce a first cDNA amplicon(s);
diluting the first amplicon(s) and performing a second PCR thereon until all primers are consumed to produce a second amplicon(s), thereby amplifying the RNA(s) of interest; wherein the first amplicon(s) are one or more of an HLA-A, an HLA-B or an HLA-DBR1, an HLA-DQA1, or an HLA-DQ-B1 cDNA(s) and the exon-specific primers shown in at least SEQ ID NO:15 and 16 and additional primer pairs selected from the group consisting of SEQ ID NOs:17-27.

18. The method of claim 17, further comprising labeling the second PCR primers with one or more fluorophores.

19. The method of claim 18, wherein the fluorophor is a cyanine dye.

20. The method of claim 18, further comprising:
hybridizing the second amplicon or set of amplicons to probes having sequences complementary to an area of interest in a gene sequence;
detecting a fluorescence pattern from the hybridized amplicon(s); and
identifying one or more genes or allelotypes thereof based on the fluorescence pattern.

21. The method of claim 20, wherein the gene(s) are one or more of an HLA-A gene, an HLA-B gene or an HLA-DRB1 gene, an HLA-DQA1 gene, or an HLA-DQB1 gene or combinations thereof.

22. The method of claim 20, further comprising sequencing the second amplicon(s) for an analysis thereof.

23. The method of claim 22, wherein analysis determines one or more of identity, paternity of an individual, forensic information, tissue matching, risk factors for the development of disease, or response to medication.

24. The method of claim 17, wherein the second PCR is linear PCR and the second amplicon(s) is cRNA(s).

25. The method of claim 17, wherein the second PCR is real time PCR and the primers are exon specific to the first cDNA amplicon(s).

26. The method of claim 17, wherein the raw sample is fresh or rehydrated and comprises unprocessed fluid blood, dried unprocessed blood, a fresh buccal swab sample, a dried buccal swab sample, fecal material, a vaginal sample or a sample obtained by swabbing an animate or inanimate surface or object.

27. A method for allelotyping a gene of interest, comprising:
obtaining a raw biological sample from one or more individuals;
performing a first PCR on the raw biological sample using primers specific to the gene locus or a defined set of gene loci to produce a first amplicon or first set of amplicons;
diluting the first amplicon or first set of amplicons and performing a second PCR with the amplicon(s) serving as the template for the second PCR reaction using primers specific to an exon or a set of exons within the gene locus until all primers are consumed to produce an amplicon set from the second PCR reaction, wherein said primers specific to the exon shown in at least SEQ ID NO:15 and 16 and additional primer pairs selected from the group consisting of SEQ ID NOs:17-27;
hybridizing the second amplicon or amplicon set to probes having sequences of allele variations associated with the gene or gene set of interest;
detecting a signal from the hybridized amplicon or amplicon set; and
assigning an allelotype based on the detected hybridization signal.

28. The method of claim 27, wherein the first amplicon or amplicon set is cDNA amplified from RNA comprising the sample and the second PCR is linear PCR or real time PCR performed thereon.

29. The method of claim 27, wherein the signal is fluorescence, said second PCR primer pairs labeled with one or more fluorophores.

30. The method of claim 29, wherein the fluorophor is a cyanine dye.

31. The method of claim 27, wherein the gene of interest is one or more of an HLA-A gene, an HLA-B gene or an HLA-DRB1 gene, an HLA-DQA1 gene, or an HLA-DQB1 gene or combinations thereof.

32. The method of claim 27, wherein the locus-specific primers have sequences shown in SEQ ID NOS: 1-14.

33. The method of claim 27, wherein the raw biological sample is fresh or rehydrated and comprises blood, dried blood, a buccal sample, fecal matter or a vaginal sample or other sample obtained by swabbing an animate surface or object.

34. The method of claim 27, wherein the individuals comprise a population in a field environment.

* * * * *